(12) United States Patent
Kierny et al.

(10) Patent No.: US 10,059,937 B2
(45) Date of Patent: Aug. 28, 2018

(54) METHOD AND KIT FOR GENERATING HIGH AFFINITY BINDING AGENTS

(71) Applicant: The Board of Trustees of the University of Illinois, Urbana, IL (US)

(72) Inventors: Michael Kierny, Chicago, IL (US); Brian Kay, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 167 days.

(21) Appl. No.: 14/917,691

(22) PCT Filed: Sep. 26, 2014

(86) PCT No.: PCT/US2014/057617
§ 371 (c)(1),
(2) Date: Mar. 9, 2016

(87) PCT Pub. No.: WO2015/048391
PCT Pub. Date: Apr. 2, 2015

(65) Prior Publication Data
US 2016/0222376 A1    Aug. 4, 2016

Related U.S. Application Data

(60) Provisional application No. 61/883,547, filed on Sep. 27, 2013, provisional application No. 61/988,559, (Continued)

(51) Int. Cl.
*C40B 30/04*   (2006.01)
*C12N 15/10*   (2006.01)

(52) U.S. Cl.
CPC ..... *C12N 15/1058* (2013.01); *C12N 15/1037* (2013.01); *C12N 15/1041* (2013.01); *C40B 30/04* (2013.01)

(58) Field of Classification Search
None
See application file for complete search history.

(56) References Cited

U.S. PATENT DOCUMENTS

| 6,818,418 B1 | 11/2004 | Lipovsek et al. | 435/69.1 |
| 2006/0177862 A1 | 8/2006 | Osbourn et al. | 435/5 |

(Continued)

FOREIGN PATENT DOCUMENTS

| WO | WO 2006/114700 A2 | 11/2006 |
| WO | WO 2010/036856 A2 | 4/2010 |
| WO | WO 2010/036860 A2 | 4/2010 |

OTHER PUBLICATIONS

Extended European Search Report issued in EP 14848541.0 dated Apr. 26, 2017.

(Continued)

*Primary Examiner* — Christian C Boesen

(57) ABSTRACT

A combined ribosome-display and phage-display method and kit for carrying out the method are provided. The method includes screening a ribosome-display library of binding agents to identify binding agents that interact with one or more target molecules of interest, converting the RNA encoding the binding agents to a phage-display format by amplification and primer extension, and the screening the phage-display library to enrich for binding agents that interact with one or more target molecules of interest.

4 Claims, 5 Drawing Sheets

Specification includes a Sequence Listing.

Related U.S. Application Data filed on May 5, 2014, provisional application No. 61/991,121, filed on May 9, 2014.

(56) References Cited

U.S. PATENT DOCUMENTS

| | | | |
|---|---|---|---|
| 2010/0113304 A1* | 5/2010 | Hufton | C12N 15/1037 506/14 |
| 2010/0152063 A1 | 6/2010 | Cappuccilli et al. | 506/17 |
| 2013/0210680 A1 | 8/2013 | Derda et al. | 506/26 |

OTHER PUBLICATIONS

Huang et al. "Improvements to the Kunkel Mutagenesis Protocol for Constructing Primary and Secondary Phage-Display Libraries" Methods 2012 58:10-17.

Kierny, M. "Generating Recombinant Affinity Reagents by Phage- and Ribosome-Display" Thesis, University of Illinois at Chicago Dec. 1, 2014 pp. 1-225.

Dower et al. "High efficiency transformation of *E. coli* by high voltage electroporation" Nucleic Acids Res. 1988 16:6127-6145.

Dufner et al. "Harnessing phage and ribosome display for antibody optimization" Trends Biotechnol. 2006 24:523-9.

Finlay et al. "Affinity maturation of a humanized rat antibody for anti-RAGE therapy: comprehensive mutagenesis reveals a high level of mutational plasticity both inside and outside the complementarity-determining regions" J. Mol. Biol. 2009 388:541-558.

Groves et al. "Affinity maturation of phage display antibody populations using ribosome display" J. Immunol. Methods 2006 313:129-139.

Groves & Nickson "Affinity maturation of phage display antibody populations using ribosome display" Methods Mol. Biol. 2012 805:163-90.

Hanes & Pluckthun "In vitro selection and evolution of functional proteins by using ribosome display" Proc. Natl. Acad. Sci. USA 1997 94:4937-4942.

Koide et al. "The fibronectin Type III domain as a scaffold for novel binding proteins" J. Mol. Biol. 1998 284:1141-1151.

Ling "Large antibody display libraries for isolation of high-affinity antibodies" Comb. Chem. High Throughput Screen 2003 6:421-432.

Pelletier et al. "An in vivo library-versus-library selection of optimized protein-protein interactions" Nat. Biotechnol. 1999 17:683-690.

Pluckthun "Ribosome display: a perspective" Methods Mol. Biol. 2012 805:3-28.

Sheets et al. "Efficient construction of a large nonimmune phage antibody library: the production of high-affinity human single-chain antibodies to protein antigens" Proc. Natl. Acad. Sci. USA 1998 95:6157-6162.

Vaughan et al. "Human antibodies with sub-nanomolar affinities isolated from a large non-immunized phage display library" Nat. Biotechnol. 1996 14:309-314.

International Search Report and Written Opinion in PCT/US14/57617 dated Dec. 22, 2014.

International Preliminary Report on Patentability in PCT/US14/57617 dated Mar. 29, 2016.

* cited by examiner

SEQUENCE LISTING

<160> NUMBER OF SEQ ID NOS: 17

<210> SEQ ID NO 1
<211> LENGTH: 94
<212> TYPE: PRT
<213> ORGANISM: Artificial sequence
<220> FEATURE:
<223> OTHER INFORMATION: Synthetic polypeptide

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 2
<211> LENGTH: 94
<212> TYPE: PRT
<213> ORGANISM: Artificial sequence
<220> FEATURE:
<223> OTHER INFORMATION: Synthetic polypeptide

<400> SEQUENCE: 2

Met Ala Val Ser Asp Val Pro Arg Lys Leu Glu Val Val Ala Ala Thr
1               5                   10                  15

Pro Thr Ser Leu Leu Ile Ser Trp Asp Ala Pro Cys Arg Lys Cys Leu
            20                  25                  30

Tyr Tyr Arg Ile Thr Tyr Gly Glu Thr Gly Gly Asn Ser Pro Val Gln
        35                  40                  45

Glu Phe Thr Val Pro Gly Ser Lys Ser Thr Ala Thr Ile Ser Gly Leu
    50                  55                  60

Lys Pro Gly Val Asp Tyr Thr Ile Thr Val Tyr Ala Val Thr Arg Leu
65                  70                  75                  80

Glu Phe Ile Ser Lys Pro Ile Ile Ser Ile Asn Tyr Arg Ile
                85                  90

<210> SEQ ID NO 3
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 3
atacgaaatt aatacgactc actataggga gaccacaacg g                              41

<210> SEQ ID NO 4
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 4

```
ccgcacacca gtaaggtgtg cggtttcagt tgccgctttc tttct          45
```

<210> SEQ ID NO 5
<211> LENGTH: 8
<212> TYPE: PRT
<213> ORGANISM: Artificial sequence
<220> FEATURE:
<223> OTHER INFORMATION: Synthetic peptide

<400> SEQUENCE: 5

Asp Tyr Lys Asp Asp Asp Asp Lys
1               5

<210> SEQ ID NO 6
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 6

```
gccgctggta cggtagttaa tcgag                                25
```

<210> SEQ ID NO 7
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 7

```
atggccgttt ctgatgttcc gcgta                                25
```

<210> SEQ ID NO 8
<211> LENGTH: 90
<212> TYPE: PRT
<213> ORGANISM: Artificial sequence
<220> FEATURE:
<223> OTHER INFORMATION: Synthetic polypeptide

<400> SEQUENCE: 8

Met Ala Val Ser Asp Val Pro Arg Lys Leu Glu Val Val Ala Ala Thr
1               5                   10                  15

Pro Thr Ser Leu Leu Ile Ser Trp Asp Gln Asp Gln Val Tyr Tyr Tyr
            20                  25                  30

Arg Ile Arg Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Thr Ser Tyr
65                  70                  75                  80

Ala Tyr Ile Ile Ser Ile Asn Tyr Arg Ile
                85                  90

<210> SEQ ID NO 9
<211> LENGTH: 96
<212> TYPE: PRT
<213> ORGANISM: Artificial sequence
<220> FEATURE:
<223> OTHER INFORMATION: Synthetic polypeptide

<400> SEQUENCE: 9

Met Ala Val Ser Asp Val Pro Arg Lys Leu Glu Val Val Ala Ala Thr

-continued

```
                1               5                  10                  15
        Pro Thr Ser Leu Leu Ile Ser Trp Asp Pro Tyr Trp Phe Ser Gly Leu
                        20                  25                  30

Tyr Tyr Arg Ile Thr Tyr Gly Glu Thr Gly Gly Asn Ser Pro Val Gln
                        35                  40                  45

Glu Phe Thr Val Pro Gly Ser Lys Ser Thr Ala Thr Ile Ser Gly Leu
                    50                  55                  60

Lys Pro Gly Val Asp Tyr Thr Ile Thr Val Tyr Ala Val Thr Tyr Tyr
        65                  70                  75                  80

Ser Trp Gly Tyr Leu Val Gly Glu Ile Ile Ser Ile Asn Tyr Arg Ile
                            85                  90                  95

<210> SEQ ID NO 10
<211> LENGTH: 15
<212> TYPE: PRT
<213> ORGANISM: Artificial sequence
<220> FEATURE:
<223> OTHER INFORMATION: Synthetic peptide

<400> SEQUENCE: 10

Lys Lys Phe Glu Leu Leu Pro Thr Pro Pro Leu Ser Pro Ser Tyr
1               5                   10                  15

<210> SEQ ID NO 11
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: PHOSPHORYLATION

<400> SEQUENCE: 11

Lys Lys Phe Glu Leu Leu Pro Thr Pro Pro Leu Ser Pro Ser Tyr
1               5                   10                  15

<210> SEQ ID NO 12
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION

<400> SEQUENCE: 12

Lys Lys Phe Glu Leu Leu Pro Thr Pro Pro Leu Ser Pro Ser Tyr
1               5                   10                  15

<210> SEQ ID NO 13
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: PHOSPHORYLATION
```

```
<220> FEATURE:
<221> NAME/KEY: MOD_RES
<222> LOCATION: (8)..(8)
<223> OTHER INFORMATION: PHOSPHORYLATION

<400> SEQUENCE: 13

His Thr Gly Phe Leu Thr Glu Tyr Val Ala Thr Arg Trp
1               5                   10

<210> SEQ ID NO 14
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION

<400> SEQUENCE: 14

Glu Ala Arg Ser Arg Asp Ala Thr Pro Pro Val Ser Pro Ile Asn Tyr
1               5                   10                  15

Lys

<210> SEQ ID NO 15
<211> LENGTH: 75
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (29)..(43)
<223> OTHER INFORMATION: n represents a, c, t, or g
<220> FEATURE:
<221> NAME/KEY: misc_feature
<222> LOCATION: (44)..(52)
<223> OTHER INFORMATION: n is present or absent and when present
      represents a, c, t, or g

<400> SEQUENCE: 15
cggtttcacc gtacgtgata cggtaatann nnnnnnnnnn nnnnnnnnnn nnatcccagc      60
tgatcagcag gctag                                                      75

<210> SEQ ID NO 16
<211> LENGTH: 95
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (26)..(46)
<223> OTHER INFORMATION: n represents a, c, t, or g
<220> FEATURE:
<221> NAME/KEY: misc_feature
<222> LOCATION: (47)..(64)
<223> OTHER INFORMATION: n is present or absent and when present
      represents a, c, t, or g

<400> SEQUENCE: 16
cgctggtacg gtagttaatc gagatnnnnn nnnnnnnnnn nnnnnnnnnn nnnnnnnnnn      60
nnnnagtaac agcgtataca gtgatggtat agtca                                95
```

```
<210> SEQ ID NO 17
<211> LENGTH: 68
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (19)..(27)
<223> OTHER INFORMATION: n represents a, c, t, or g
<220> FEATURE:
<221> NAME/KEY: misc_feature
<222> LOCATION: (28)..(42)
<223> OTHER INFORMATION: n is present or absent and when present
      represents a, c, t, or g

<400> SEQUENCE: 17
gccgctgatg gtagcagtnn nnnnnnnnnn nnnnnnnnnn nnatcaggta cagtgaactc    60
ctgaaccg                                                            68
```

US 10,059,937 B2

METHOD AND KIT FOR GENERATING HIGH AFFINITY BINDING AGENTS

This application is the U.S. national stage of PCT International Application No. PCT/US2014/057617, filed Sep. 26, 2014, which claims the benefit of priority of U.S. Provisional Application No. 61/883,547, filed Sep. 27, 2013; U.S. Provisional Application No. 61/988,559, filed May 5, 2014; and U.S. Provisional Application No. 61/991,121, filed May 9, 2014, the contents of each of which are incorporated herein by reference in their entireties.

INTRODUCTION

This invention was made with government support under grant number U54 DK093444 awarded by the National Institutes of Health. The government has certain rights in the invention.

BACKGROUND

It has been shown that the larger the starting library diversity, the more likely a high affinity reagent will be selected without the need for affinity maturation (Vaughan, et al. (1996) *Nat. Biotechnol.* 14:309-314; Ling (2003) *Comb. Chem. High Throughput Screen* 6:421-432). However, due to the limited number of *E. coli* cells that can be feasibly grown, the largest libraries constructed for phage-display are on the order of $1 \times 10^{10}$ members (Dower, et al. (1988) *Nucleic Acids Res.* 16:6127-6145; Sheets, et al. (1998) *Proc. Natl. Acad. Sci. USA* 95:6157-6162), which are stored frozen and subjected to freeze-thaw before selection. Ribosome-display, on the other hand typically starts with a freshly translated library with a diversity 100-fold greater (Pluckthun (2012) *Methods Mol. Biol.* 805:3-28; Hanes & Pluckthun (1997) *Proc. Natl. Acad. Sci. USA* 94:4937-4942), but requires more steps and effort if not automated.

Ribosome-display is described in US 2006/0177862 for use in the selection of antibodies, wherein ribosome-display complexes are encapsidated into a viral coat to protect the product from degradation. Further, US 2013/0210680 suggests the use of ribosome-display in amplifying a library of clones. Moreover, ribosome-display has been combined with other display technologies for screening the output from the ribosome-display rounds (Pelletier, et al. (1999) *Nat. Biotechnol.* 17:683-690) or for affinity maturation of phage-display selected pools (Groves, et al. (2006) *J. Immunol. Methods* 313:129-139; Groves & Nickson (2012) *Methods Mol. Biol.* 805:163-90; Finlay, et al. (2009) *J. Mol. Biol.* 388:541-558; Dufner, et al. (2006) *Trends Biotechnol.* 24:523-9). However, ribosome-display has not been integrated with phage-display as part of a primary selection scheme.

SUMMARY OF THE INVENTION

The present invention is a method for generating a high affinity agent to a target molecule, which combines comprising ribosome-display and phage-display methodologies. The method of the invention includes the steps of obtaining a ribosome-display library comprising nucleic acids encoding a population of binding agents; screening the ribosome-display library for binding agents that bind to one or more target molecules; amplifying nucleic acids encoding the binding agents that bind to the one or more target molecules; annealing the amplified nucleic acids to a phage-display vector comprising nucleic acids encoding at least a portion of the binding agent; primer extending the annealed nucleic acids to generate a phage-display library; and screening the phage-display library to identify phage clones that bind to the one or more target molecules.

A kit for generating high affinity monobodies is also provided, which includes a first population of BC loop oligonucleotides; a second population of FG loop oligonucleotides; a ribosome-display vector harboring nucleic acids encoding FN3 and a bacteriophage origin of replication; a phage-display vector harboring nucleic acids encoding FN3; and reagents for primer extension and ligation. In some embodiments, the kit further includes a third population of DE loop oligonucleotides.

DETAILED DESCRIPTION OF THE INVENTION

Figure 1:
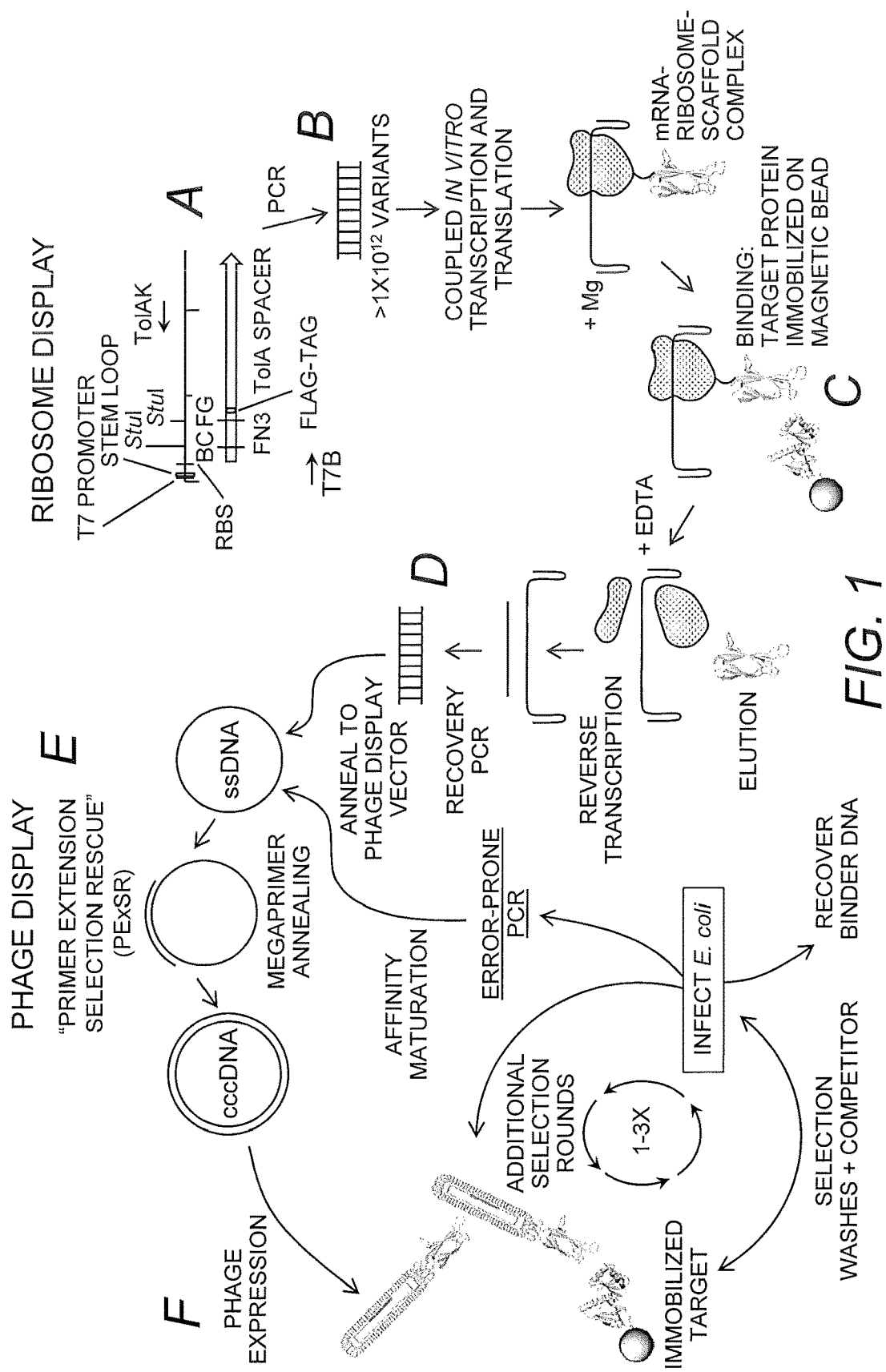
FIG. 1 shows a schematic of steps A-F of the primer extension for selection rescue (PExSR) method of the invention. The procedure starts with a large dsDNA template made by PCR, which contains the T7 promoter, ribosome binding site (RBS), monobody scaffold, TolA tether and the 5' and 3' hairpins (Step A). The template is added to the coupled in vitro transcription and translation kit to allow the mRNA-ribosome-nascent monobody scaffold complex to form (Step B). The complex is then subjected to a selection for a given biotinylated target molecule. The target molecule and complex are captured by streptavidin-coated magnetic beads and washed, the complex is dissociated with EDTA, and the mRNA is reverse transcribed (Step C). The cDNA is PCR-amplified using primers inside of the antibody scaffold (Step D). As a unique feature of this invention, the PCR product (functioning as a megaprimer) is annealed to a ssDNA phage-display vector containing a M13 origin of replication and a pIII phage coat protein, the megaprimer is extended to fill in the remaining plasmid to form a heteroduplex dsDNA, the plasmid is transformed into *E. coli* and the phage are expressed (Step E). Phage-display commences for 1-3 additional rounds of selection where the binders are recovered and screened or affinity matured through error-prone PCR, megaprimer annealing, and increased stringency selections (Step F).

An efficient method for generating high quality affinity reagents has now been developed, which combines protein display technologies, ribosome-display and phage-display (Table 1). The method, referred to herein as Primer Extension Selection Rescue or PExSR, takes advantage of the large diversity possible with DNA libraries by conducting the first round of selection by ribosome-display. The output from the first round is then converted to a phage-display format using megaprimer annealing and extension to a single-stranded uracilated DNA phagemid, wherein the parental strand is destroyed upon transformation into *E. coli* (Kunkel (1985) *Proc. Natl. Acad. Sci. USA* 82:488-492; Sidhu, et al. (2000) *Meth. Enzymol.* 328:333-363; Huang, et al. (2012) *Methods* 58:10-17). The resulting recombinant proteins are then expressed on phage and subjected to additional rounds of off-rate selection (FIG. 1, steps A-F). A particular advantage of the instant method is in the multiplexing ability of the procedure, which continues to increase, and the efficiency in generating single-digit nanomolar binding reagents in a few days.

TABLE 1

| | Ribosome-Display | Phage-Display | PExSR |
|---|---|---|---|
| Starting Library Size | $10^{12}$-$10^{13}$ | $10^{9}$-$10^{10}$ | $10^{12}$-$10^{13}$ |
| Hours per round | 30 | 11 | 15 |
| Average hours per day | 7.5 | 5.5 | 6 |
| Steps per round | 14 | 9 | 10.5 |
| Affinity Kd values | nM to pM | μM to nM | nM to pM |
| Affinity Maturation | Integrated | Separate Selection | Integrated |
| Library Stability | Freshly made protein | Protein stored frozen | Protein made fresh |
| Regenerate Stability | PCR | Grow Liters of Cells | PCR |
| Antibody Bias | Minimal | Phage Expression | Reduced |

Using the method of this invention, monobodies were generated, which were some of the tightest binding reagents of the FN3 scaffold generated without an extensive and laborious mRNA selection scheme (Xu, et al. (2002) *Chem. Biol.* 9:933-942) or through affinity maturation (Gilbreth, et al. (2008) *J. Mol. Biol.* 381:407-418; Koide, et al. (2012) *J. Mol. Biol.* 415:393-405). In addition, identifiable binders were generated after a single round of ribosome-display. As such, the instant method is rapid, simple and produces high quality binding reagents for use in diagnostic, therapeutic and research applications.

Accordingly, the present invention provides a method for by generating high affinity agents to target molecules by obtaining a ribosome-display library containing nucleic acids encoding a population of binding agents; screening the ribosome-display library for binding agents that bind to one or more target molecules; amplifying nucleic acids encoding the binding agents, which bind to the one or more target molecules; annealing the amplified nucleic acids to a phage-display vector containing nucleic acids encoding at least a portion of the binding agent; primer extending the annealed nucleic acids to generate a phage-display library; and screening the phage-display library to identify a phage clone that binds to the one or more target molecules. An exemplary embodiment of the instant method is illustrated in FIG. 1.

A binding agent of this invention refers to protein that has a high affinity for, and specifically binds to, a target molecule, e.g., an antigen. As used herein, the term "affinity" refers to the non-random interaction of two molecules. Affinity, or the strength of the interaction, can be expressed quantitatively as a dissociation constant ($K_D$). Binding affinity can be determined using standard techniques. In particular embodiments, the binding agents of this invention have a high affinity for a target molecule, with $K_D$s in the range of low μM (e.g., 1-10 μM) to nM, or more preferably in the range of nM to pM.

Binding agents in accordance with this invention are proteins and include, but are not limited to, well-known antibodies and antibody fragments such as Fab and Fd fragments, single-domain antibodies, Forkhead-Associated (FHA) domains, monobodies, minibodies, single-chain variable fragments (scFv), AFFIBODY molecules, affilins, anticalins, DARPins (i.e., designed ankyrin repeat proteins), and nanofitins (also known as affitins). Other binding agents that can be generated using this method include receptors, enzymes, peptides and protein ligands. In certain embodiments, the binding agent is a single chain molecule and/or monomeric. Desirably, the binding agent of the invention is in the range of 20 to 400 amino acid residues in length, or more desirably 60 to 300 amino acid residues in length. Moreover, the binding agent is preferably thermal stable, lacks cysteine residues, can be expressed via a recombinant expression system (e.g., *E. coli*), has a known three-dimensional structure, has uniform biochemical properties among variants, and can bind to an array of target molecules.

Single-domain antibodies or nanobodies are antibody fragments composed of a single monomeric variable antibody domain (Harmsen & De Haard (2007) *Appl. Macrobiol. Biotechnol.* 77:13-22). Like a whole antibody, it is able to bind selectively to a specific antigen. Single-domain antibodies are typically ~110 amino acid residues long and can be derived from heavy-chain antibodies found in camelids (i.e., $V_HH$ fragments) or cartilaginous fish (i.e., $V_{NAR}$). An alternative approach is to split the dimeric variable domains from common IgG from humans or mice into monomers (Holt, et al. (2003) *Trends Biotechnol.* 21:484-490). As with antibodies, the CDRs of nanobodies can be modified to alter the specificity of the nanobodies.

The Forkhead-Associated domain is a phosphopeptide recognition domain found in many regulatory proteins (Hofmann & Buchner (1995) *Trends Biochem. Sci.* 20:347-9). FHA domains are approximately 65-100 amino acid residues and display specificity for phosphothreonine-containing epitopes, but can also recognize phosphotyrosine with relatively high affinity. The FHA domain forms an 11-stranded β-sandwich that has a short α-helix inserted between β strands 2 and 3 and an α-helical region at the extreme C-terminus. The peptide binding site is created by the loop regions between β 3/4, β 4/5, and β 6/7 (Durocher, et al. (2000) *Mol. Cell* 6:1169-1182), which can modified to alter specificity and affinity.

Monobodies, also known as Adnectins, are 94 amino acid proteins, which are based upon the structure of human fibronectin, in particular the tenth extracellular type III domain of fibronectin. This domain, referred to as the FN3 scaffold, has a structure similar to antibody variable domains, with two β-sheets, one constituted by β-strands A, B and E, and the other by β-strands C, D, F and G (Koide & Koide (2007) *Methods Mol. Biol.* 352:95-109). The specificity of monobodies can be tailored by modifying the loops BC (between the second and third beta sheets) and FG (between the sixth and seventh sheets) (Koide, et al. (1998) *J. Mol. Biol.* 284:1141-51). An exemplary FN3 monobody scaffold has the amino acid sequence:

```
VSDVPRDLEV VAATPTSLLI SWDAPAVTVR YYRITYGETG

GNSPVQEFTV PGSKSTATIS GLKPGVDYTI

TVYAVTGRGD SPASSKPISI NYRT
```

(SEQ ID NO:1), wherein BC and FG loops are unlined. See U.S. Pat. No. 6,818,418). Another exemplary FN3 monobody scaffold includes the sequence:

```
MAVSDVPRKL EVVAATPTSL LISWDAPCRK CLYYRITYGE

TGGNSPVQEF TVPGSKSTAT ISGLKPGVDY

TITVYAVTRL EFISKPIISI NYRI
```

(SEQ ID NO:2), wherein BC and FG loops are unlined.

A minibody scaffold, which is related to the immunoglobulin fold, is a protein generated by deleting three beta strands from a heavy chain variable domain of a monoclonal antibody (Tramontano, et al. (1994) *J. Mol. Recognit.* 7:9). This protein includes 61 residues and can be used to present two hypervariable loops. In some embodiments, a minibody is a homodimer, wherein each monomer is a single-chain variable fragment (scFv) linked to a human IgG1 CH3 domain by a linker, such as a hinge sequence.

Single-chain variable fragments (scFv) are fusion proteins composed of the variable regions of the heavy ($V_H$) and light ($V_L$) chains of immunoglobulins, which are connected by a short linker peptide of ten to about 25 amino acid residues. The linker is usually rich in glycine for flexibility, as well as serine or threonine for solubility, and can either connect the N-terminus of the $V_H$ with the C-terminus of the $V_L$, or vice versa. As with antibodies, the CDRs of scFv molecules can be modified to alter the specificity of the scFv.

Affibody molecules are small proteins (e.g., 58 amino acid residues) with a three-helix bundle domain, originally based upon the Z domain of staphylococcal protein A (Ståhl & Nygren (1997) *Pathol. Biol.* (Paris) 45:66-76; Nilsson, et al. (1987) *Prot. Eng.* 1:107-133; and U.S. Pat. No. 5,143,844). Based on the Z protein as a basic structure or scaffold, mutagenesis of surface-exposed amino acids can be carried out to create variants with an altered binding affinity. See, U.S. Pat. No. 6,534,628; Nord, et al. (1995) *Prot. Eng.* 8:601-608; Nord, et al. (1997) *Nat. Biotech.* 15:772-777.

Affilins are proteins that are structurally derived from human gamma-B crystallin or ubiquitin. The binding region of affilins is located in a beta sheet (Ebersbach, et al. (2007) *J. Mol. Biol.* 372:172-185; Vijay-Kumar, et al. (1987) *J. Mol. Biol.* 194:531-44), such that modification of near-surface amino acid residues of these proteins alters specificity. In particular, the near surface amino acids 2, 4, 6, 15, 17, 19, 36 and 38 of gamma crystalline are typically modified (see, WO 01/04144), whereas residues 2, 4, 6, 62, 63, 64, 65 and 66 of ubiquitin are typically modified (see, WO 2006/040129).

Anticalins are artificial proteins derived from lipocalins, which can bind to either proteins or small molecules (Weiss & Lowman (2000) *Chem. Biol.* 7:547-554). Lipocalins of use in this invention include, but are not limited to the bilin-binding protein (BBP) from *Pieris brassicae* (Beste, et al. (1999) *Proc. Natl. Acad. Sci. USA* 96:1898-1903; Schmidt & Skerra (1994) *Eur. J. Biochem.* 219:855-863; Schlehuber, et al. (2000) *J. Mol. Biol.* 297:1105-1120) and bovine retinol-binding protein (RBP) (Berni, et al. (1990) *Eur. J. Biochem.* 192:507-513). Anticalins have a barrel structure formed by eight antiparallel β-strands pairwise connected by loops. Sixteen 16 amino acid residues, distributed across the four loops, form the binding site, which can be mutagenized to modify affinity and selectivity (Skerra (2008) *FEBS J.* 275:2677-83).

DARPins derived from ankyrin proteins are composed of at least three, usually four or five repeat motifs, and have a molecular mass of about 14 to 18 kDa. Using a combination of sequence and structure consensus analyses, a amino acid residue ankyrin repeat module with seven randomized positions has been developed as a binding agent (Binz, et al. (2003) *J. Mol. Biol.* 332:489-503).

Nanofitins are 66 amino acid residue proteins derived from the DNA binding protein Sac7d of *Sulfolobus acidocaldarius* (EP 2469278). The binding area of nanofitins is located on the surface and is composed of 14 residues (i.e., residues 7-9, 21, 22, 24, 26, 29, 31, 33, 40, 42, 44, and 46), which can be modified to alter specificity (Mouratou, et al. (2007) *Proc. Natl. Acad. Sci. USA* 104:17983-8).

In accordance with one embodiment of the present invention, nucleic acids encoding the binding agent are introduced into a ribosome-display vector and subsequently subjected to classic primer extension mutagenesis using mutagenesis primers (i.e., megaprimers), thereby generating a naïve ribosome-display library. In an alternative embodiment, a ribosome-display library can be generated from a previously selected binding agent to further enhance binding. For example, an FHA domain, generated by phage-display, can be introduced into the ribosome-display format to create more diversity through error-prone PCR (Zaccolo, et al. (1996) *J. Mol. Biol.* 255:589-603) or mutagenic PCR (Cadwell & Joyce (1994) *PCR Methods Appl.* 3:S136-S140). Ribosome-display vectors are well-known in the art and include vectors suitable for prokaryotic or eukaryotic display system. A prokaryotic ribosome-display system is also referred to as polysome display system.

A ribosome-display vector of the invention typically includes a promoter or RNA polymerase binding sequence, a ribosome binding site, a translation initiation sequence, a nucleic acid encoding an amino acid spacer sequence separating the expressed displayed binding agent from the ribosome after translation to assist correct folding of the binding agent. Optionally, the ribosome-display vector may also include one or more sequences encoding detection tags, 3' stem loop structure and/or 5' stem loop structure to protect synthesized mRNA, a translation enhancer or "activator"

sequence(s). In a particular embodiment, the ribosome-display vector includes a bacteriophage origin of replication (e.g., an M13 origin of replication) for single-strand DNA production. Exemplary origins of replication are provided under GENBANK Accession Nos. J02465 (M13 origin of replication) and M10869 (f1 origin of replication).

The promoter or RNA polymerase binding sequence suitable for the invention may include any promoters suitable for in vitro translation. Exemplary promoters include, but are not limited to, T7, T3, or SP6 promoters, or any sequences recognized by RNA polymerases T7, T3 or SP6. In some embodiments, a ribosome-display vector of the invention may include two promoters, such as both the T7 and SP6 promoters. A ribosomal binding site may be positioned upstream, downstream or within the promoter region. This ribosome binding site may be specific for prokaryotic ribosomal complexes, for example a Shine-Dalgamo sequence, if a prokaryotic translation procedure is used.

Suitable prokaryotic translation systems include are known in the art and commercially available. The ribosome binding site may also be specific for a eukaryotic translation system, for example a Kozak consensus sequence, if a eukaryotic translation procedure is used. A suitable eukaryotic translation system includes, but is not limited to, the rabbit reticulocyte system (Krawetz, et al. (1983) *Can. J. Biochem. Cell. Biol.* 61:274-286; Merrick (1983) *Meth. Enzymol.* 101:38). Additional translation enhancer sequences may also be included. For example, the translation enhancer of *X. leavis* β globin gene may be inserted between the promoter and translation initiation site. Other exemplary translation enhancers or activator sequences include, but are limited to, untranslated "leader sequences" from tobacco mosaic virus (Jobling, et al. (1988) *Nucleic Acids Res.* 16:4483-4498), 5'-untranslated region from alfalfa mosaic virus RNA 4 (Jobling & Gehrke (1987) *Nature* 325:622-625), black beetle virus (Nodavirus) RNA 2 (Friesen & Rueckert (1981) *J. Virol.* 37:876-886), and turnip mosaic virus, and brome mosaic virus coat protein mRNAs (Zagorski, et al. (1983) *Biochimie* 65:127-133).

An amino acid spacer sequence can be engineered into the nucleic acid that will be fused or linked at the C-terminus of the displayed binding agent to separate it from the ribosome upon translated. It is contemplated that the spacer sequence allows the displayed polypeptide to exit completely from the ribosome "tunnel" and to fold correctly, yet leave the translated binding agent on the ribosome due to the lack of a stop codon which essentially freezes the peptide onto the ribosome, yet still attached to the RNA from which the binding agent is translated from. Typically, a suitable spacer sequence encodes at least 20 amino acids in length. In particular, a suitable spacer length may include at least 30 amino acids, 40 amino acids, 50 amino acids, 60 amino acids, 70 amino acids, 80 amino acids, 90 amino acids, 100 amino acids. In certain embodiments, the spacer includes 23 amino acids. In certain embodiments, the spacer includes 69 amino acids. In certain embodiments, the spacer includes 16 amino acids. Suitable spacer sequences can be derived from any known protein such as, but not limited to, M13 phage pIII, the Cκ domain of a light chain of an antibody (He & Taussig (1997) *Nucl. Acids Res.* 25:5132-4), a proline-rich sequence of *E. coli* TonB, a helical segment of *E. coli* TolA (Schaffitzel, et al. (1999) *J. Immunol. Methods* 231:119-35) or λ phage protein D (Osada, et al. (2009) *J. Biochem.* 145:693-700).

A tag sequence may be incorporated into the ribosome-display vector of the invention. Typically, the tag sequence is incorporated at the N-terminus or C-terminus of the displayed binding agent. In some embodiments, the tag sequence is at the N-terminus of the translated binding agent. Suitable tags include, but are not limited to, a stretch of histidines (e.g., 5-6 histidines), an epitope recognized by an antibody, for example, substance P, a FLAG tag or c-myc tag.

The ribosome-display vector may also include a 5' and/or 3' region with palindromic sequences capable of forming a stem loop structure. The stem loop structure is believed to impede translocation, thus, palindromic sequences slow down the movement of ribosomes during translation and prevent ribosomes from "falling off" the mRNA thereby protecting synthesized mRNA and increasing the number of polysomes in the in vitro translation step. In some embodiments, the ribosome-display vector of the present invention is capable of forming a 3' stem loop structure. In some embodiments the ribosome-display of the present invention is capable of forming a 5' and a 3' stem loop structure. In addition, the 3' region may contain a poly-A or other polynucleotide stretch for later purification of the mRNA from the in vitro translation.

To facilitate transfer of the entire nucleic acid fragment encoding the binding agent, the ribosome-display vector of the present invention as described above, typically includes restriction sites, flanking the binding agent-encoding sequence. In some embodiments, the ribosome-display vector includes a first restriction site 5' of the coding region of the binding agent in the untranslated region and a second restriction site 3' downstream to the binding agent-encoding sequence. In some embodiments, the first and second restriction sites of the ribosome-display vector are the same. In other embodiments, the first and second restriction sites of the ribosome-display vector are different.

The ribosome-display vector may be chemically synthesized by protocols well-known to those skilled in the art. Alternatively, each of the above elements may be incorporated into one or more plasmids, amplified in microorganisms, purified by standard procedures, and cut into appropriate fragments with restriction enzymes before assembly into the vector. General methods for constructing ribosome-display vectors, ribosome-display libraries and method of use are described in U.S. Pat. Nos. 5,643,768; 5,658,754; 7,074,557; Mattheakis, et al. (1994) *PNAS USA* 91:9022-9026; Mattheakis, et al. (1996) *Methods Enzymol.* 267:195-207; Gersuk, et al. (1997) *Biotech Biophys. Res. Comm.* 232:578-582; Hanes & Pluckthun (1997) *PNAS USA* 94:4937-4942; and Hanes, et al. (1998) *PNAS USA* 95:14130-50. A particularly suitable ribosome-display vector, which can be modified to include nucleic acids encoding a binding agent, is pRDV (GENBANK Accession No. AY327136). An exemplary ribosome-display vector of the present invention is described in the Examples section and illustrated in FIG. 2.

As indicated, a ribosome-display library can be obtained by mutagenizing the ribosome-display vector via primer extension mutagenesis. This involves generating a single-stranded ribosome-display vector and subjecting the single-stranded ribosome-display vector to primer extension. In one embodiment, the single-stranded ribosome-display vector is produced using nicking endonucleases as know to a person skilled in the art. In certain embodiments, the ribosome-display vector is made single-stranded by rolling circle replication from a single-stranded bacteriophage origin of replication present in the ribosome-display vector. Examples of such bacteriophage include M13, fd, and f1, which normally replicate as plasmids in bacterial hosts. To facilitate packaging and purification of the single-stranded ribosome-display vector, "helper" bacteriophage can be used. Methods for preparing single-stranded vectors are well-known in the art and any suitable method can be employed.

Once a single-stranded ribosome-display vector is obtained, primer extension is carried out using mutagenesis primers or oligonucleotides, which encode a population or library of binding sites. As used herein, mutagenesis primers or oligonucleotides have a central randomized or partially randomized sequence encoding the binding site of the binding agent, which is flanked by two non-random sequences. In this respect, mutagenesis primers or oligonucleotides have the structure $R^1—X_n—R^2$, wherein $R^1$ and $R^2$ complementarity to the template molecule, X represents nucleic acids encoding the binding site, and n is the number of codons, which can range from 3 to 20 or more desirably 5 to 15. A fully randomized sequence encoding the binding site means that the each codon is represented at each position of the binding site. A partially randomized sequence means that the codons of the binding site can be biased to include codons, which have been shown to be prevalent at variable regions of affinity molecules. As indicated herein, tyrosine is often present in variable regions, as are glycine and serine, which provide flexibility for movement of the tyrosine side chain. Accordingly, in some embodiments, "X" of the mutagenesis primer is biased to include codons for tyrosine, serine and glycine. In particular embodiments, the codons of the binding site include a mixture of 30% Tyr, 15% Ser, 15% Gly, 5% Phe, 5% Trp and 2.3% each of all the other amino acids. In particular embodiments, the binding site does not include codons for Cys and Met.

The mutagenesis primers or oligonucleotides are used to prime the complementary strand synthesis of the template DNA. Annealing of the mutagenesis primers or oligonucleotides to the template DNA requires that the mutagenesis primers or oligonucleotides have enough complementarity in its 5' and 3' ends with the template molecule. Typically, there are about 15 to about 30 complementary nucleotides in the 5' end and about 15 to about 30 complementary nucleotides in the 3' end of the primer relative to the target DNA. However, shorter complementary segments may also be used, especially when one or few consecutive nucleotides are targeted for mutagenesis. Primer extension in the presence of a DNA polymerase, such as T7 or T4 polymerase, and ligation with a DNA ligase, such as T4 ligase, results in a ligated heteroduplex, i.e., covalently closed circular DNA (cccDNA), in which one stand (the template strand) is non-mutated and the other, in vitro synthesized strand, contains the desired mutations. See FIG. 3.

Depending on the number of binding sites to be mutagenized, the primer extension step of this invention can employ the use of one or more different populations of oligonucleotides. In accordance with embodiments pertaining to the use of the FN3 scaffold, mutagenesis involves the use of two populations of oligonucleotides, one spanning the BC loop (SEQ ID NO:15) and one spanning the FG loop (SEQ ID NO:16). The mutagenesis primers may be synthetic oligonucleotides or PCR products that include one or more desired substitutions, deletions, additions or any desired combination thereof. Means and methods for producing such oligonucleotides or primers are readily available in the art. Alternatively, the mutagenesis oligonucleotides or primers can include random mutations. In such cases, mutations may be introduced into the mutagenesis oligonucleotides or primers during synthesis, e.g., by means of error-prone PCR. Means and methods for obtaining such oligonucleotides or primers are known in the art. For use in primer extension, the oligonucleotides or PCR products used as primers are typically 5'-phosphorylated via an enzymatic phosphorylation reaction, by enzymatic digestion of the 5' end of the DNA or by conjugation in a chemical reaction.

While heteroduplex ribosome-display library may be directly used in a ribosome-display screen, in certain embodiments, the ribosome-display library is amplified, e.g., by conventional PCR amplification using primers, which flank the nucleic acids encoding the binding agent and amino acid spacer sequence of the ribosome-display vector. Such primers have been in the art. See, Dreier & Pluckthun ((2011) *PCR Protocols, Methods in Molecular Biology*, vol. 687, Park (ed.) Springer Sicence+Business Media LLC), which describes primer T7B (5'-ata cga aat taa tac gac tca cta tag gga gac cac aac gg-3'; SEQ ID NO:3) and primer tolAk (5'-ccg cac acc agt aag gtg tgc ggt ttc agt tgc cgc ttt ctt tct-3'; SEQ ID NO:4).

To facilitate screening of the libraries herein, certain embodiments include removal of the heteroduplex template strand. The can be achieved by restriction enzymatic digestion or using an uridylated template strand, as exemplified herein. For example, the template DNA can be replicated in the presence of uridine in an ung–/dut– *E. coli* strain, such as BW313 and CJ236, which are deficient in the enzyme dUTP pyrophosphatase (dut–) resulting in an increased incorporation of uracil in place of thymine in the DNA. Uridylated template DNA may also be prepared enzymatically using for example T7 DNA polymerase together with dNTP's and dUTP. Uridylated template DNA can then be removed by treatment with uracil-N-glycosylase (UDG), which hydrolyzes uracils in the heteroduplex.

The step of screening the ribosome-display library for binding agents that bind to one or more target molecules is carried out by transcribing the ribosome-display library to produce a pool of mRNAs; subjecting the pool of mRNAs to in vitro translation to generate the library of binding agents displayed on the ribosomes (i.e., ribosome-mRNA-binding agent complexes); and identifying binding agents that bind to the target molecule. Coupled in vitro translation/transcription systems and reactions for use in ribosome-display are well-known in the art and any suitable methodology can be used herein, including prokaryotic or eukaryotic display systems.

Binding agents in the ribosome-display library, which specifically bind to one or more target molecules, can be identified using any suitable method that detects interactions between molecules including, e.g., ELISA, co-immunoprecipitation, bimolecular fluorescence complementation, affinity electrophoresis, pull-down assays, label transfer, and the like. However, in certain embodiments, the screen is carried out using a tagged target molecule. For example, as described herein, a biotin-tagged target molecule was contacted with the library of ribosome-displayed binding agents, and binding agent-target molecule complexes were captured using streptavidin-coated magnetic beads. Advantageously, any unbound ribosome-displayed binding agents can be removed by washing the magnetic beads.

Target molecules that can be used in accordance with this invention include proteins, glycoproteins, phosphoproteins, other post-translationally modified proteins, protein complexes, nucleic acids, protein:nucleic acid complexes, carbohydrates, lipid complexes, organic and inorganic molecules, including natural and synthetic versions of any such molecules. The target or target molecules may include a single protein or other biomolecule or multiple molecules (e.g., in a multi-molecular complex). As exemplified herein, target molecules can be tagged to facilitate detection and immobilization of binding agents of interest. Such tags include, e.g., a His-tag, FLAG-tag, V5-tag, HA-tag, or c-myc-tag. In particular embodiments, the target molecule is biotinylated.

Once binding agents of interest are identified, which bind to one or more target molecules, the mRNA molecules encoding the binding agents of interest are isolated and amplified. Typically, this involves dissociating the ribosome-mRNA-binding agent complexes bound to the target molecule and amplifying the mRNA by reverse transcription and PCR. RNA isolation can be carried out using any conventional method and/or commercially available kit. Similarly, reverse transcription of mRNA into cDNA and PCR amplification are routinely practiced in the art and any suitable method and/or commercially available kit can be used in the instant method. In an alternative embodiment, the ribosome-mRNA-binding agent complexes bound to the target molecule are dissociated, the mRNA is isolated and reverse transcribed to produce cDNA, and the cDNA is cloned into a plasmid, as is conventional in the art of cDNA library synthesis.

As a unique feature of the instant method, the molecules identified in the ribosome-display library screen are subsequently converted to a phage-display format by primer extension. This step of the instant method involves using the reverse-transcribed/PCR-amplified molecules encoding the binding agents of interest as megaprimers in Kunkel mutagenesis (Kunkel, et al. (1991) *Methods Enzymol.* 204:125-139; Huang, et al. (2012) *Methods* 58:10-17) to prime DNA synthesis with a uracilated phage-display vector as a template. In particular, the megaprimers are annealed to nucleic acids of the phage-display vector that encode at least a portion of the binding agent (e.g., the non-random sequences used in the ribosome-display vector). The reverse-transcribed/PCR-amplified molecules or megaprimers in this step are phosphorylated, annealed to uracilated phage-display vector, extended in the presence of a DNA polymerase (e.g., T7 or T4 polymerase) and ligated with a DNA ligase (e.g., T4 ligase) to generate a heteroduplex phage-display library in which one stand (the template strand) is non-mutated and the other, in vitro synthesized strand, contains the desired mutations.

A phage-display vector of the present invention is a vector containing phage-derived polynucleotide sequences capable of expressing, or conditionally expressing, a heterologous polypeptide, for example, as a fusion protein with a phage protein (e.g., a phage surface protein). In some embodiments, a phage-display vector of the present invention is a vector derived from a filamentous phage (e.g., phage f1, fd, and M13) or a bacteriophage (e.g., T7 bacteriophage or a lambdoid phage. Filamentous phage and bacteriophage are described by, e.g., Santini ((1998) *J. Mol. Biol.* 282:125-135), Rosenberg, et al. ((1996) *Innovations* 6:1-6), and Houshmand, et al. ((1999) *Anal. Biochem.* 268:363-370).

In general, a phage-display vector of the invention can include the following elements: a promoter suited for constitutive or inducible expression (e.g., lac promoter); a ribosome binding site and signal sequence preceding the sequence encoding a displayed peptide; and one or more restriction sites; optionally, a tag sequence such as a stretch of 5-6 histidines or an epitope recognized by an antibody; a second tag sequence; a suppressible codon (e.g., a termination codon); and a sequence encoding a phage surface protein positioned in-frame to form a fusion with the binding agent to be displayed. In general, a phage-display vector of the invention contains a promoter and/or regulatory region operably linked to a polynucleotide sequence encoding the binding agent and a sequence encoding a phage surface protein.

The term "operably linked" refers to a functional linkage between nucleic acid sequences such that the linked promoter and/or regulatory region functionally controls expression of the coding sequence. It also refers to the linkage between coding sequences such that they may be controlled by the same promoter and/or regulatory region. Such linkage between coding sequences may also be referred to as being linked in-frame or in the same coding frame such that a fusion protein comprising the amino acids encoded by the coding sequences may be expressed.

In other embodiments of the invention, the ability of the phage-display vector to express a fusion protein is regulated in part by use of a regulated promoter or other regulatory region (e.g., an inducible promoter such that in the absence of induction, expression is low or undetectable). Non-limiting examples of inducible promoters include the lac promoter, the lac UV5 promoter, the arabinose promoter, and the tet promoter. In some embodiments, an inducible promoter can be further restricted by incorporating repressors (e.g., lacI) or terminators (e.g., a tHP terminator). For example, repressor lacI can be used together with the Lac promoter.

As used herein, the term "phage surface protein" refers to any protein normally found at the surface of a filamentous phage (e.g., phage f1, fd, and M13) or a bacteriophage (e.g., λ, T4 and T7) that can be adapted to be expressed as a fusion protein with a heterologous polypeptide and still be assembled into a phage particle such that the polypeptide is displayed on the surface of the phage. Suitable surface proteins derived from filamentous phages include, but are not limited to, minor coat proteins from filamentous phages, such as gene III proteins and gene VIII proteins; major coat proteins from filamentous phages such as, gene VI proteins, gene VII proteins, gene IX proteins; gene 10 proteins from T7; and capsid D protein (gpD) of bacteriophage λ. In some embodiments, a suitable phage surface protein is a domain, a truncated version, a fragment, or a functional variant of a naturally occurring surface protein. For example, a suitable phage surface protein can be a domain of the gene III protein, e.g., the anchor domain or "stump." Additional exemplary phage surface proteins are described in WO 00/71694. As appreciated by the skilled artisan, the choice of a phage surface protein is to be made in combination with a consideration of the phage-display vector and the cell to be used for propagation thereof.

Any peptide sequences capable of driving or directing secretion of expressed protein or polypeptide can be used as signal sequence for the phage-display vector of the invention. Exemplary leader sequences include, but not limited to, a PelB leader sequence and an OmpA leader sequence. In addition, a fusion polypeptide can optionally, include a tag that may be useful in purification, detection and/or screening. Suitable tags include, but not limited to, a FLAG-tag, polyhistidine-tag, a gD-tag, a c-myc tag, green fluorescence protein tag, a GST-tag or β-galactosidase tag.

General methods for constructing phage-display vectors, phage-display libraries and the method of use are described, for example, in U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard, et al. (1999) *J. Biol. Chem.* 274:18218-30; Hoogenboom, et al. (1998) *Immunotechnoloqy* 4:1-20; Hoogenboom, et al. (2000) *Immunol, Today* 2:371-8; Fuchs, et al. (1991) *Bio/Technol-* ogy 9:1370-1372; Huse, et al. (1989) *Science* 246:1275-1281; Griffiths, et al. (1993) *EMBO J.* 12:725-734; Hawkins, et al. (1992) *J. Mol. Biol.* 226:889-896; Clackson, et al. (1991) *Nature* 352:624-628; Gram, et al. (1992) *PNAS* 89:3576-3580; Garrard, et al. (1991) *Bio/Technology* 9:1373-1377; Rebar, et al. (1996) *Methods Enzymol.* 267: 129-49; Hoogenboom, et al. (1991) *Nucl. Acid Res.* 19:4133-4137; and Barbas, et al. (1991) *PNAS* 88:7978-7982. Exemplary phage-display vectors of the invention are described in the Example section.

Once prepared, the phage-display library is subsequently screened to identify phage clones that bind to the one or more target molecules. The phage-display library screening step is carried out by inducing the phage to display the binding agents on the surface of the phage clones and identifying binding agents that bind to the target molecule. As in the ribosome-display screening step, any suitable method that detects interactions between molecules can be used to identify binding agents of interest including, e.g., ELISA, co-immunoprecipitation, bimolecular fluorescence complementation, affinity electrophoresis, pull-down assays, label transfer, and the like. However, in certain embodiments, the screen is carried out using a tagged target molecule as described above.

The present method may be used to create a library of binding agents, such as monobodies or single-domain antibodies. The method of the invention is suitable for conducting multiple rounds of phage-display to enrich for binding agents with a high affinity (see Example 5). In this respect, additional mutagenesis steps can be included, e.g., error-prone PCR, to add more diversity through random mutation. Moreover, stringent selection (i.e., reduced amounts of Target and/or off-rate selection through the addition of excess soluble Target) can be included to recover higher affinity binding agents. Further, the instant method finds application in a multiplex format to select binding agents to multiple, distinct target molecules (see Example 6 and FIGS. 5 and 6). In addition to specificity and affinity, binding agents can be screened and selected for improved solubility, protein folding, thermal stability and crystallization.

As described herein, the method of the present invention can be adapted to generate any type of binding agent. However, in particular embodiments, the instant method is used in the generation of a high affinity monobody. In accordance with this embodiment, the method includes the steps of (a) annealing a first population of oligonucleotides and a second population of oligonucleotides, each encoding a library of binding sequences, to a single-stranded ribosome-display vector comprising nucleic acids encoding a monobody scaffold; (b) primer extending the first population of oligonucleotides and second population of oligonucleotides to generate heteroduplexes, wherein one strand of the heteroduplex encodes the monobody scaffold comprising the library of binding sequences; (c) amplifying both strands of the heteroduplexes; (d) subjecting the amplified products of step (c) to in vitro transcription and in vitro translation to produce ribosome-mRNA-monobody scaffold complexes; (e) contacting the ribosome-mRNA-monobody scaffold complexes with one or more tagged target molecules to bind the ribosome-mRNA-monobody scaffold complexes to the tagged target molecules; (f) removing unbound ribosome-mRNA-monobody scaffold complexes; (g) dissociating the ribosome-mRNA-monobody scaffold complexes bound to the tagged target molecules; (h) reverse transcribing the mRNA molecules of (g) to generate cDNA; (i) amplifying the cDNA molecules of (h) with primers that anneal to nucleic acids encoding the monobody scaffold to generate amplified nucleic acids encoding the monobody scaffold and binding sequences; (j) annealing the amplified nucleic acids of (i) to a phage-display vector comprising nucleic acids encoding the monobody scaffold; (k) primer extending the annealed nucleic acids of (j) to generate heteroduplexes, wherein one strand of the heteroduplex encodes the monobody scaffold and binding sequences; (l) expressing the monobody scaffold and binding sequences encoded by the phage-display vector; (k) screening the expressed products of (l) with one or more of the tagged target molecules thereby generating a high affinity monobody to the one or more target molecules.

To facilitate the practice of the present method, this invention also provides a kit for generating high affinity monobodies. The kit includes at least two populations of oligonucleotides, at least one for generating a library of binding sequences at the BC loop of FN3 and at least a second for generating a library of binding sequences at the FG loop of FN3. In some embodiments, the DE loop is also modified. In this respect, a third population of oligonucleotides encoding the DE loop of FN3 can be included. Thus, the kit of the invention provides embodiments including a combination of BC loop oligonucleotides, FG loop oligonucleotides and/or DE loop oligonucleotides. For example, oligonucleotide combinations can include BC+FG, BC+DE, FG+DE or BC+FG+DE. DE loop oligonucleotides of this invention can have the structure:

(SEQ ID NO: 17)
5'-GCC GCT GAT GGT AGC AGT $N_{3-8}$ ATC AGG TAC AGT GAA CTC CTG AAC CG-3', wherein $N_{3-8}$ represents a mixture of codons encoding 3, 4, 5, 6, 7, and 8 amino acid residues.

In particular embodiments, the oligonucleotides are those provided in SEQ ID NO:15, SEQ ID NO:16 and/or SEQ ID NO:17. In addition, the kit includes a ribosome-display vector harboring nucleic acids encoding FN3 and a bacteriophage origin of replication (e.g., M13); and a phage-display vector harboring nucleic acids encoding FN3. Moreover, the kit includes reagents for primer extension and ligation including a DNA polymerase without significant strand displacement activity (e.g., T7 or T4 DNA polymerase), dNTP's, a DNA ligase (e.g., T4 ligase), ATP and DTT in appropriate reaction/storage buffers. The kit may further include helper phage (e.g., M13K07) for generating a single-strand ribosome-display vector, restriction enzymes, primers (e.g., T7B and tolAk primers of SEQ ID NOs:3 and 4, respectively; and/or Reverse and Forward PExSR FN3 primers of SEQ ID NO:6 and 7, respectively) and PCR reagents (e.g., Taq, dNTP, $MgCl_2$ and buffer) for PCR amplification, reagents for reverse transcription, a biotin labeling kit, strepavidin-coated magnetic beads, in vitro transcription and translation reagents, DNA and RNA purification columns, wash solutions, elution solutions and/or competent cells for transformation.

The following non-limiting examples are provided to further illustrate the present invention.

EXAMPLE 1

Materials and Methods

Figure 2:
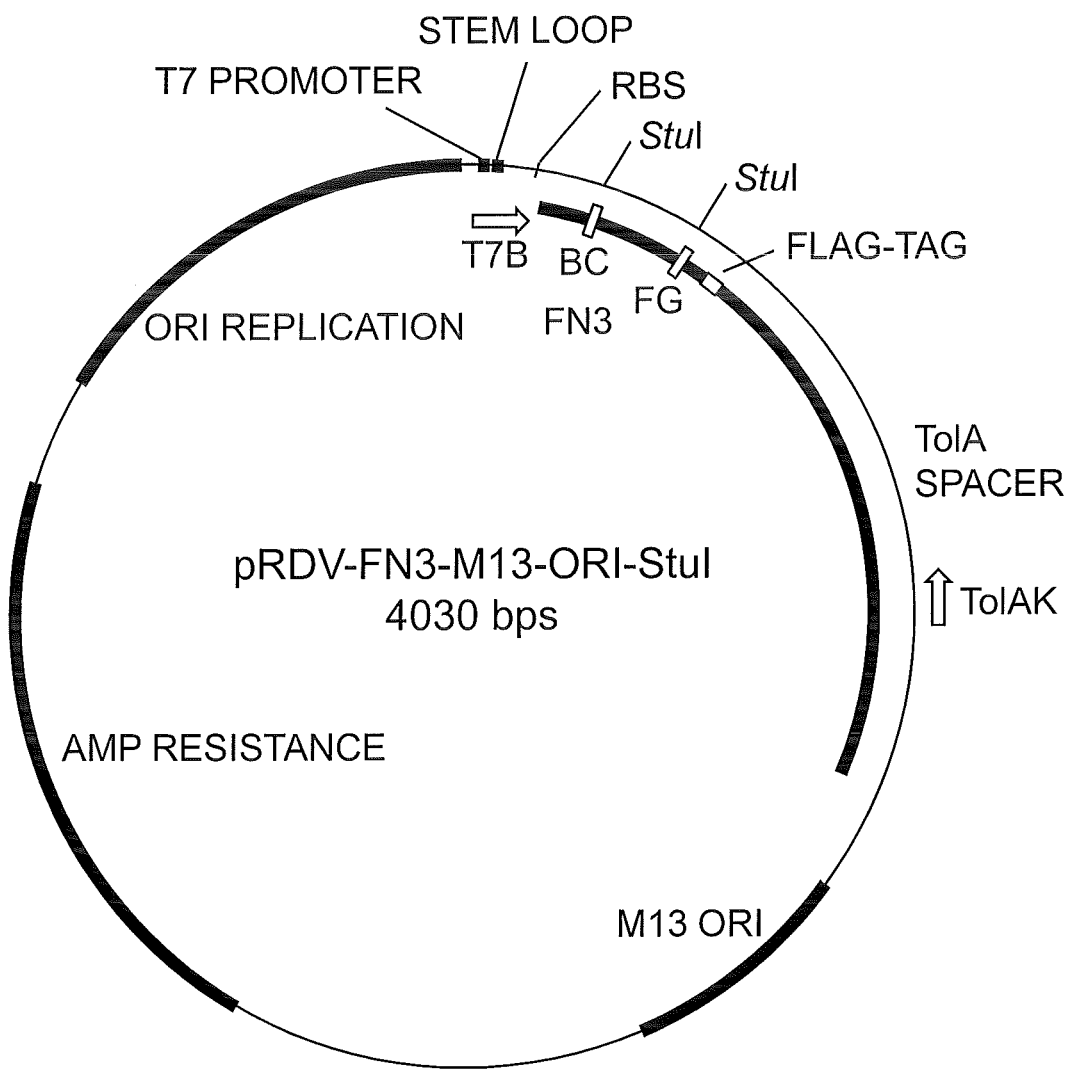
FIG. 2 depicts an exemplary PExSR ribosome-display plasmid. The pRDV plasmid was modified to contain a M13 origin of replication. The FN3 (tenth extracellular type III domain of fibronectin) scaffold was cloned downstream of the T7 promoter, 5' stem loop and the RBS. The scaffold contains two StuI restriction sites within the two variable loop regions BC and FG along with TAA stop codons. A FLAG-tag was introduced between the FN3 and the TolA spacer protein. The forward primer, T7B, and the reverse primer, TolAk, are for amplifying the template for ribosome-display.

PExSR Ribosome-Display Library Plasmid. The ribosome-display vector pRDV (GENBANK Accession No. AY327136) was modified from the original vector to contain a M13 origin of replication (bps 1539-1748, for ssDNA production) and a Fibronectin III (FN3) monobody scaffold (bps 117-401) containing a down-stream FLAG tag (bps 402-434, DYKDDDDK; SEQ ID NO:5) (FIG. 2). The FN3 scaffold also contained StuI restriction sites and ochre stop codons in the BC and FG variable loops to prevent the parent clone from displaying a full protein. The TolA tether protein is downstream and in-frame with the FN3 coding region and FLAG epitope. Its purpose is to allow the FN3 to emerge from the ribosomal tunnel so it may freely interact with antigen.

Single-Stranded DNA Production. The pRDV-FN3-StuI plasmid was electroporated into CJ236 electrocompetent cells with genotype: FΔ(HindIII)::cat(Tra+Pil+CamR)/ung-1 relA1 dut-1 thi-1 spoT1 mcrA (New England Biolabs). Cells were grown to mid-log phase in 2×YT/15 µg/mL Chloramphenicol (Cm)/50 µg/mL Carbenicillin (Cb) and infected with M13K07 helper phage (New England Biolabs) at a multiplicity of infection (MOI) of 10 for 1 hour at 37° C. The phage were allowed to express overnight (~22 hours) in 2×YT/Cb/50 µg/mL Kanamycin (Kan) at 25° C., 230 rpm shaking. After pelleting the cells, the phage particles were precipitated with 4% $PEG_{8000}$ and 0.5 M NaCl, final concentrations, at room temperature for 20 minutes. The resulting phage particle pellet was resuspended in 4 mL of PBS. The phage particles were lysed and the ssDNA purified using the QIAPREP Spin M13 Kit (Qiagen). The ssDNA was eluted in 50° C. water and the concentration determined by NANODROP spectrophotometer (Thermo Scientific).

Trinucleotide Library Synthesis. The oligonucleotides for the primer extension were a mixture of triplet phosphoramidite codons (Ella Biotech, Munich, Germany) inserted into a scaffold sequence, wherein the insert encoded 30% tyrosine, 15% serine, 15% glycine, and 5% of tryptophan and phenylalanine. The remaining residues were represented at 2.3% each except for cysteine and methionine, which are excluded. The lengths of the loops were also varied at 5, 6, 7, and 8 residues for the BC loop and 7, 9, 10, 11, 12, and 13 residues for the FG loop. The BC loop oligonucleotides had the structure:

(SEQ ID NO: 15)
5'-CGG TTT CAC CGT ACG TGA TAC GGT AAT $AN_{5-8}$ ATC
CCA GCT GAT CAG CAG GCT AG-3', wherein $N_{5-8}$ represents the mixture of codons encoding 5, 6, 7, and 8 amino acid residues. The FG loop oligonucleotides had the structure:

(SEQ ID NO: 16)
5'-CGC TGG TAC GGT AGT TAA TCG AGA $TN_{7-13}$ AGT AAC
AGC GTA TAC AGT GAT GGT ATA GTC A-3', wherein $N_{7-13}$ represents the mixture of codons encoding 7, 9, 10, 11, 12, and 13 amino acid residues.

Primer Extension. Primer extension was carried out according to known methods (Huang, et al. (2012) *Methods* 58:10-17). Briefly, about 300 pmol of the loop primers were phosphorylated with T4 polynucleotide kinase (New England Biolabs) for 1 hour then allowed to anneal to 100 pmol of the ssDNA pRDV-FN3-StuI by denaturing at 95° C. for 2 minutes and slowly reducing temperature at 1° C. per minute until 24° C. was reached. To fill in the remaining portions of the plasmid, the heteroduplex was extended by T7 DNA Polymerase (New England Biolabs) and T4 DNA Ligase (New England Biolabs). The double-stranded hetero-duplex (closed-complementary DNA or cccDNA) results in the recombinant sequence as the coding strand and the parent sequence as the antisense strand.

Phage-TolA Recombinant Confirmation. To determine the recombination rate in order to add sufficient amounts of cccDNA to the PCR and maintain diversity, a small amount of the heteroduplex DNA (~10 ng) was sacrificed for transformation into TG-1 *E. coli* cells and plated on 2×YT/Cb to obtain single colonies. From the overnight plates, 96 colonies were grown in 250 µL of 2×YT/Cb in a 96-deep-well plate at 280 rpm, 37° C., for 3.5 hours. When the cells reached mid-log phase ($OD_{600}$=0.4), they were infected with M13K07 helper phage at an MOI of 10 for 1 hour with 150 rpm shaking at 37° C. The cells were spun down and resuspended in 400 µL 2×YT/Cb/Kan and grown overnight for phage expression at 30° C. After 16 hours, the FN3-FLAG-TolA fusion protein was induced through the T7 promoter with 1 mM IPTG (Isopropyl β-D-1-thiogalactopyranoside) by adding 100 µL 2×YT/Cb/Kan, 5 mM IPTG, to all wells and allowing expression for 5 hours.

In parallel, a MAXISORP 96-well microtiter plate (Nunc) was coated overnight at 4° C. with 10 µg/mL NEUTRAVIDIN (Life Technologies) in Phosphate-Buffered Saline (PBS). The day of the ELISA, the wells were blocked with 200 µL of 1% casein in PBS for 1 hour (Thermo Scientific). All washings were done in 300 µL of PBST (PBS+0.1% TWEEN 20), three times each, using a BIOTEK ELx405 plate washer. After washing, 50 µL of 1:5000 biotin labeled-anti-FLAG antibody (Sigma-Aldrich) in PBST was added to all wells for 1 hour.

The overnight culture with the 5 hours IPTG induction was spun down at 4,000 rpm for 5 minutes and 50 µL of the supernatant added to the prepared 96-well MAXISORP plate, which was incubated with 500 rpm shaking for 1 hour. A small amount of fusion protein was assumed to have been secreted into the supernatant, and therefore, lysing of the cells was unnecessary. The plate was washed and 50 µL of 1:5000 anti-M13-HRP monoclonal antibody (GE Healthcare Life Sciences) added to all wells for 1 hour. The plate was washed five times with PBST and substrate 2,2-azino-bis(3-ethylbenorthiazoline-6-Sulfonic Acid (ABTS; Sigma-Aldrich) with 0.03% $H_2O_2$ was added. The plate was read at an absorbance 405 nm after 5, 15, and 30 minutes using a POLARSTAR OPTIMA microplate reader (BMG Labtech).

Ribosome-Display Template. To generate the ribosome-display template, PCR was performed for 185×50 µL reactions, which amplified both the recombinant and the parent strands of the FN3 monobody. The primers used were: T7B (5'-ata cga aat taa tac gac tca cta tag gga gac cac aac gg-3'; SEQ ID NO:3) and Tol Ak (5'-ccg cac acc agt aag gtg tgc ggt ttc agt tgc cgc ttt ctt tct-3'; SEQ ID NO:4). Each reaction contained 1 µg of cccDNA, 0.4 mM dNTPs, 1 µM primers, 3 mM $MgCl_2$, 1× polymerase buffer and 1 U of PLATINUM Taq DNA Polymerase (Life Technologies). Thermal cycling was performed as follows: 3 minutes at 95° C., 30 cycles of 95° C. denature for 30 seconds, 55° C. annealing for 30 seconds, and 72° C. extension for 45 seconds; and a final extension for 5 minutes at 72° C. To rid the preparation of the parental strand, the reactions were pooled and 192×60 µL restriction digests were carried out with 10 Units/reaction of StuI for 3 hours at 37° C. The digests were pooled and a phenol:chloroform:isoamyl 25:24:1 (Sigma-Aldrich) extraction was performed followed by an ethanol precipitation.

The digest was separated on a 0.8% agarose gel and the recombinant, un-digested bands, were extracted to give a yield of 54 pmol or about $3.2×10^{13}$ molecules. To maintain the diversity, but amplify the library for use in many selections, the product was amplified in 50 reactions by PCR using the same primers and conditions as before. After PCR product purification using a QIAGEN PCR Purification kit, the template DNA was concentrated by ethanol precipitation and resuspension in a small volume to ~2 µg/µL. This high concentration was necessary because of reaction volume limits in the in vitro transcription and translation kit (New England Biolabs) and the intention to add >1×10$^{13}$ library members to each selection.

PExSR Selection for MAP2K5. Target proteins were purchased from the Structural Genomics Consortium (SGC). Proteins came in formats lacking and including an N-terminal AVITAG for site-specific biotinylation. All proteins had an N-terminal 6x-His tag for immobilized metal affinity chromatography (IMAC). The target protein was a human protein kinase, Mitogen Activated Protein Kinase Kinase 5 (MAP2K5).

Ribosome-Display. Ribosome-display was carried out according to known methods (Dreier & Pluckthun (2011) *Methods Mol. Biol.* 687:283-306). The in vitro transcription and translation (IVTT) were conducted in parallel using the cell-free PUREXPRESS kit (New England Biolabs), which contained purified *E. coli* translation components and a ribosome concentration of 2.4 µM or 60 pmols per reaction, which was 3.6×10$^{13}$ molecules. The IVTT was performed for 2 hours at 30° C. using 11 µg or 1.4×10$^{13}$ molecules of the template. The reaction was stopped by the addition of 1 mL of Tris-Buffered Saline (TBS) with 0.1% TWEEN 20 (TBST), 0.5% BSA, 50 mM MgAc, 12.5 µL 200 mg/mL Heparin (Sigma). The reaction was spun down at 4° C. for 5 minutes.

All steps were carried out in a 4° C. refrigerator to reduce the amount of RNA degradation by slowing the RNase activity. A mini-centrifuge was used to briefly spin down the liquid in the tubes for all steps. For all steps, 2 mL EPPENDORF LoBind tubes were used to reduce DNA template carry-over.

Preselection: The Ribosome-mRNA-FN3 complex (500 µL) was added to two 2 mL tubes containing 30 µL of DYNABEADS MYONE T1 streptavidin-coated magnetic beads (Life Technologies) pre-blocked with TBST and 0.5% BSA. The tubes were rotated at 4° C. for 1 hour and subsequently placed into a 50 mL conical for protection from RNase contamination and ease of handling.

The beads were captured by magnetic separation and the supernatant containing the complex was added to blocked 2 mL tubes. To the +Target tube was added 100 nM (50 pmols) of biotin-MAP2K5 (16.2 kDa) in TBST. To both tubes was also added 100 mM dithiothreitol (DTT; final concentration of 0.5 mM) to prevent disulfide bond formation and dimerization of binders. Tubes were incubated with rotating for 1 hour at 4° C.

The complexes, with and without Target, were then added to separate tubes of 30 µL fresh streptavidin-coated magnetic beads blocked in TBST+0.5% BSA and incubated for 30 minutes at 4° C. with tumbling. The bead-ribosome-mRNA-FN3 complex was washed once in 1 mL of cold wash buffer (TBST, 50 mM MgAc, 0.1% BSA) and transferred to a new blocked tube. The beads were then washed eight additional times with 1 mL wash buffer with five minutes of tumbling each at 4° C. During the final wash, the beads were transferred to a new blocked tube to obtain a cleaner elution. This removed any DNA or complexes bound to the tube walls.

The complex was eluted into 100 µL of elution buffer (TBST, 0.5% BSA, 25 mM EDTA, 50 µg/mL of *S. cerevisiae* RNA) for 10 minutes at 4° C. This was added to 400 µL of Lysis Buffer of the High Pure RNA Isolation kit (Roche Applied Science) and shaken to mix. The previous step was repeated with fresh elution buffer (100 µL) for an additional 10 minutes and then added to the 500 µL of elution and lysis buffer on ice with mixing.

RNA Isolation. The lysis/elution was spun in the High Pure RNA Isolation kit column at 8,000×g for 1 minute. The flow-through was removed. One hundred microliters of diluted DNase I at 1.8 U/µL in DNase incubation buffer was added to each ±Target column and incubated for 15 minutes at room temperature. Five hundred microliters of Wash Buffer I was added and the column was centrifuged for 1 minute at 8,000×g. Columns were washed again with 500 µL of Wash Buffer II and centrifuged at 8,000×g for 1 minute. Another 100 µL of Wash Buffer II was added to the column, which was subsequently centrifuged at 13,000×g for 2 minutes. Recovered RNA was eluted in 50 µL of Elution Buffer (PCR-grade water) and incubated for 2 minutes before centrifugation at 8,000×g for 1 minute into clean tubes. The +Target RNA elution (4×12.5 µL) and −Target elution (2×12.5 µL) were transferred to individual PCR tubes. The RNA was denatured at 70° C. for 10 minutes and kept on ice until the Reverse Transcription step.

Reverse Transcription. To generate cDNA, the ±Target elutions were reverse-transcribed using Reverse Transcriptase (+RT). As a control, one reaction from each set was performed without Reverse Transcriptase (−RT). Each of the reactions had a 20.25 µL final volume and included the following: 1.23 µM inside Reverse Primer PExSR FN3 (5'-gcc get ggt acg gta gtt aat cga g-3'; SEQ ID NO:6), 0.25 mM dNTPs, 1 U/µL of RIBOLOCK RNase inhibitor (Thermo Scientific), ±1.23 U/µL AFFINITYSCRIPT Multiple Temperature Reverse Transcriptase (RT) (Agilent Technologies), 1× Affinity Transcript Buffer, and 9.9 µM DTT. Three +RT reactions were performed with the eluted RNA from the +Target tube to obtain the most cDNA for the downstream PCR. The −Target and −RT control reactions were performed once each. All reactions were incubated at 50° C. for 1 hour.

cDNA Amplification by PCR. To amplify the cDNA, 10 µL of each reverse transcription reaction were used in a 35 cycle PCR. The PCR reaction, with a total volume of 50 µL, included the following: 0.5 µL HERCULASE II Polymerase Fusion DNA Polymerase (Agilent Technologies), 1× HERCULASE II Reaction buffer, 0.1 mM dNTPS, 5% dimethyl sulfoxide (DMSO), 1 µM inside Forward Primer PExSR FN3 (5'-atg gcc gtt tct gat gtt ccg cgt a-3'; SEQ ID NO:7), and 1 µM inside Reverse Primer PExSR FN3. Four reactions were performed for the +Target, +RT to generate a sufficient amount of template for the primer extension. PCR was performed as follows: 3 minutes at 95° C.; 30 cycles of 95° C. denaturation for 30 seconds, annealing at 55° C. for 30 seconds, extension at 72° C. for 45 seconds; and a final extension for 5 minutes at 72° C. The reactions were purified with the QIAQUICK PCR Purification kit and eluted in 50° C. water.

Primer Extension for Selection Recovery. The primer extension was performed in accordance with known methods (Huang, et al. (2012) *Methods* 58:10-17). Briefly, 15 pmol of the PCR product was phosphorylated for 1 hour at 37° C. The phosphorylated PCR product was annealed to 5 pmol of uracilated ssDNA phagemid pKP300-FN3-2×StuI (ssDNA phagemid expressed from M13 phage grown in CJ236 *E. coli* that lacked the Uracil Deglycosylase enzyme) by denaturing at 95° C. for 2 minutes and slowly reducing the temperature by 1° C. per minute until 24° C. was reached. To fill in the remaining portions of the plasmid, the heteroduplexes were extended by the action of T7 DNA Polymerase (New England Biolabs) and T4 DNA Ligase (New England Biolabs). The resulting double-stranded DNA was purified on a QIAQUICK column and transformed by electroporation into 2×100 µL of the TG-1 strain of *E. coli* cells (Genotype: [F′ traD36 proAB laclqZ ΔM15] supE thi-1 Δ(lac-proAB) Δ(mcrB-hsdSM)5(rK−mK−; Lucigen Corporation). Cells were allowed to recover at 150 rpm in 2 mL of warmed Recovery Media (Lucigen) for 30 minutes at 37° C. Cells were plated on two large 2×YT/Cb agar plates and incubated overnight at 30° C.

Phage-Display. Each plate was scraped into 5 mL of 2×YT media and the cells were combined and vortexed. Fifty microliters was used to inoculate 50 mL of 2×YT/Cb and grown to mid-log phase ($OD_{600}$=~0.4). Cells were infected with M13K07 helper phage at an MOI of 10 for 30 minutes at 37° C. Cells were spun down at 4,000 rpm for 7 minutes and resuspended in 2×YT/CB/Kan media. The culture was shaken at room temperature for 18 hours. The overnight culture was spun down twice at 12,000 rpm for 10 minutes and the 50 mL supernatant was precipitated with 10 mL of 24% PEG, 3 M NaCl, and 4% PEG (final), for 20 minutes at room temperature. The precipitate was spun down at 12,000 rpm for 10 minutes to pellet the phage. The tubes were rinsed with 1 mL of PBS each, and the pellet was resuspended in 1 mL of PBS.

Selection: As a de-selection step, 0.5 mL of the phage resuspension was added to 20 µL of prewashed and blocked streptavidin MAGNESPHERE magnetic beads (Promega) in an EPPENDORF LoBind 2 mL tube and tumbled for 1 hour at room temperature. The beads were captured on a magnetic separator and the phage supernatant transferred to a fresh BSA-blocked 2 mL tube. To the phage supernatant was added 10 pmol or (20 nM final) of the target biotin-MAP2K5. The mixture was allowed to equilibrate for 1 hour at room temperature with tumbling. A 10-fold concentration of competitor (MAP2K5-His-tagged protein) was added at 200 nM (100 pmol total) and allowed to equilibrate for 2 hours at room temperature with tumbling. The phage, target, and competitor mix were added to 30 µL of pre-blocked SA magnetic beads for 30 minutes to capture the biotin-MAP2K5 and bound virions. This was washed twice with 1 mL PBST for 5 minutes each, 2 minutes on the magnetic separator, then transferred to fresh a tube and wash six additional times with PBST. The final wash was transferred to a fresh tube and eluted into 100 ~L of 100 mM Glycine (pH 2) for 10 minute. The magnetic beads were captured and the elution neutralized with 12 µL of 2 M Tris, pH 10. The eluted phage were added to 1 mL of TG-1 cells grown to $OD_{600}$ of 0.4, for 30 minutes at 37° C. The cells were plated on large 2×YT/Cb plates and incubated overnight at 30° C.

For the second round of phage-display, the selection steps were repeated starting with the scraping of the cells from the plates. Cells were pooled and grown overnight after M13K07 infection. For this round, 100-fold competitor (2 µM final) was added to the phage and biotin target. Washes were performed as described above. However, the final two washes included the 100-fold competitor and 10 minute incubation for each. After two additional washes, the phage were eluted, neutralized, used to infect TG-1 cells, and plated for single colonies on 2×YT/Cb.

Multiplex Selection. The multiplex selection was performed similar to the selection against MAP2K5 with the following exceptions. The IVTT during the ribosome-display was increased to three reactions with 33.0 µg (71.61 pmol, $4.3×10^{13}$ molecules) of template in a single volume to increase the number of FN3 monobody variants exposed to three target proteins. The target proteins added to the single volume were 50 nM (50 pmols) of biotin-USP11, biotin-COPS5, and biotin-CDK2 in TBST (150 pmols Target total). After the PExSR, the selections were separated with a low stringency phage-display round. The following two rounds of phage-display increased competitor concentration from 10-fold over the Target to 100-fold over the Target. The final round of 100-fold competition was performed overnight (~22 hours) at 4° C., before elution and infection of TG-1 cells. The USP11 target competition steps were done slightly different from the other two targets due to lack of material. There was not enough non-biotinylated USP11 protein available for the in-solution competitions. To solve this, the phage and biotin-USP11 were first bound to the streptavidin magnetic beads. The empty sites not occupied by the biotinylated USP11, were filled with the addition of 1 µM free biotin. The competition was then performed with the addition of the 10-fold or 100-fold excess of biotin-USP11.

Polyclonal ELISA. Starting from the frozen, scraped cells stored in 16% glycerol at −80° C., 5 µL were thawed and used to inoculate 5 mL of 2×YT/Cb. Cultures were grown at 37° C., 250 rpm until mid-log ($OD_{600}$=~0.4). The cells were infected with M13K07 Helper phage at a MOI of 10 for 1 hour with shaking at 150 rpm, 37° C. The cells were subsequently spun down at 4,000 rpm for 5 minutes and resuspended in 50 mL of 2×YT/Cb/Kan and grown overnight for ~22 hours at 23° C., 230 rpm.

MAXISORP 96-well microtiter plates were coated overnight with 1 µg/mL NEUTRAVIDIN (Thermo Scientific) at 4° C. The plates were blocked the next day with 200 µL of 1% casein blocking buffer in PBS (Thermo Scientific) for 1 hour. All washings were carried out in 300 µL of PBST, three times each, using a BIOTEK ELx405 plate washer. Plates were washed before addition of 50 µL of 1-10 nM biotinylated targets in PBST for 1 hour with 500 rpm shaking. Plates were washed and the phage culture spun down for 5 minutes at 4,000 rpm and the supernatant diluted 1:1 with PBST before adding a total of 50 µL/well. This was incubated for 1 hour shaking. Plates were washed and 50 µL/well of 1:5000 anti-M13-HRP bacteriophage monoclonal antibody (GE HealthCare) in PBST was added to all wells for 1 hour with shaking. The final wash was performed 5 times and to each well was added 50 µL of the ABTS with 0.03% $H_2O_2$. Plates were read at absorbance 405 nm after 5, 15, and 30 minutes using a POLARSTAR OPTIMA microplate reader (BMG Labtech).

Monoclonal ELISA. The monoclonal ELISA was performed similarly to the polyclonal ELISA. For every Target, 95 colonies were picked from the final selection round and grown in deep-96-well plates with 200 µL of 2×YT media and Cb for 3 hours at 37° C., 250 rpm shaking. Each culture was infected with M13K07 Helper phage at an MOI of 10, for 30 minutes, 150 rpm shaking at 37° C. These were spun down and resuspended in 400 µL of 2×YT/Cb/Kan, and grown overnight at 23° C., 230 rpm shaking.

Biotinylated targets were added to appropriate wells in 50 µL volumes at 0.5-1 nM. Background plates with no Target protein were also used for each Target where only NEUTRAVIDIN was immobilized. Phage were spun down and the supernatant diluted 1:1 (50 µL total) in PBST when adding to each well.

Competition ELISA. The amount of phage supernatant used was optimized depending on the individual binders. Each phage supernatant was mixed with final concentrations of 100, 10, 1, 0.1, 0.01 nM free His-Only-tagged Target for 1 hour in PBST. This was added to 2 nM biotin-Target immobilized on NEUTRAVIDIN-coated NUNC MAX- ISORP plates for 1 hour and allowed to equilibrate. Phage were detected with addition of anti-M13-HRP and read at 405 nm after addition of ABTS substrate as described above. The graphing software OriginPro 9.0 (OriginLab) was used to construct the graphs. The curve fitting was performed using the "Dose Response" function under the sigmoidal fit module.

Seamless Ligation Cloning Extract (SliCE) Cloning into pET14b. For further characterization of the monobodies, the coding sequences were cloned into a SUMO fusion bacterial expression vector with a T7 promoter (pET14b-SUMO). This was performed by the in vitro recombination method known as SliCE (Zhang, et al. (2012) Nucleic Acids Res. 40:e55). Briefly, the plasmid was linearized by a single restriction enzyme, StuI, and purified by agarose gel electrophoresis. This was mixed with a PCR amplicon of the FN3 monobody clone, which contained ends that were homologous to the desired insertion location in the linearized plasmid. Addition of extract from E. coli strain DH10B and incubation at 37° C. for 1 hour allowed for electroporation into BL-21 E. coli and recovery on 2×YT/Cb plates.

Expression and Purification. Bacterial BL-21 frozen stocks of the clones in the pET14b-SUMO plasmid were inoculated into 200 mL of Overnight Express Autoinduction Media (EMD Millipore) and grown at 30° C. for 22-24 hours. Cells were centrifuged at 4,000 rpm for 10 minutes, the supernatant removed, and the pellet frozen at −80° C. The cells were thawed and resuspended in 25 mL of equilibration buffer (50 mM sodium phosphate, 300 mM sodium chloride, pH 7.4). The cells were cooled on ice with COMPLETE EDTA-Free protease inhibitor (Roche). Cell lysing was performed with 50% amplitude sonication on ice with 10 seconds ON sonication and 10 seconds OFF, for five minutes total ON time using a SONIC DISMEMBERATOR (Branson inc. Model 500). Tubes were spun at 15,000 rpm for 15 minutes. The supernatant was transferred to a 50 mL protein purification column. The agarose was prepared by washing 300-500 µL of CLONTECH His60 agarose bead slurry (60 mg/mL binding capacity) twice with equilibration buffer. Resin was added to cleared lysate in columns, the ends sealed, and the columns incubated at 4° C. for 2 hours with tumbling. The columns were then drained through the matrix and the beads washed with 150 mL of equilibration buffer until the flow through gave an $A_{280}$ NANODROP 1000 reading of <0.01 mg/mL. The column was then washed with 100 mL of wash buffer (50 mM sodium phosphate, 300 mM sodium chloride, pH 7.4, 40 mM imidazole) until again the $A_{280}$<0.01 mg/mL. The protein was eluted into 1 mL fractions using elution buffer (50 mM sodium phosphate, 300 mM sodium chloride, pH 7.4, 300 mM imidazole. The concentrations were determined using the NANODROP 1000. The $A_{280}$ protein module utilized the molecular weight and extinction coefficient parameters to obtain the most accurate determination of concentration. Purity was analyzed by SDS-PAGE.

Isothermal Titration Calorimetry (ITC). ITC was performed on a MICROCAL iTC200 system (GE Healthcare Life Sciences). Both monobody and Target were dialyzed overnight at 4° C. in 5 L of 200 mM imidazole, 150 mM NaCl, 25 mM Tris. Protein concentrations were determined by NANODROP $A_{280}$. The sample cell contained 200 µL of the Target protein at 8-24 µM and the 40 µL of titrant monobody in the syringe was 68-237 µM. A total of 21 injections were performed. The first injection volume was 0.5 µL with 200 seconds between injections. The remaining 20 injection volumes were 1.8 µL for 3.6 seconds with 200 seconds between injections and a reference power of 10 µcal/s. Heat change was plotted using the Origin 8.5 software. Measurements were taken during three separate runs and averaged.

EXAMPLE 2

FN3 Library Construction

Figure 3:
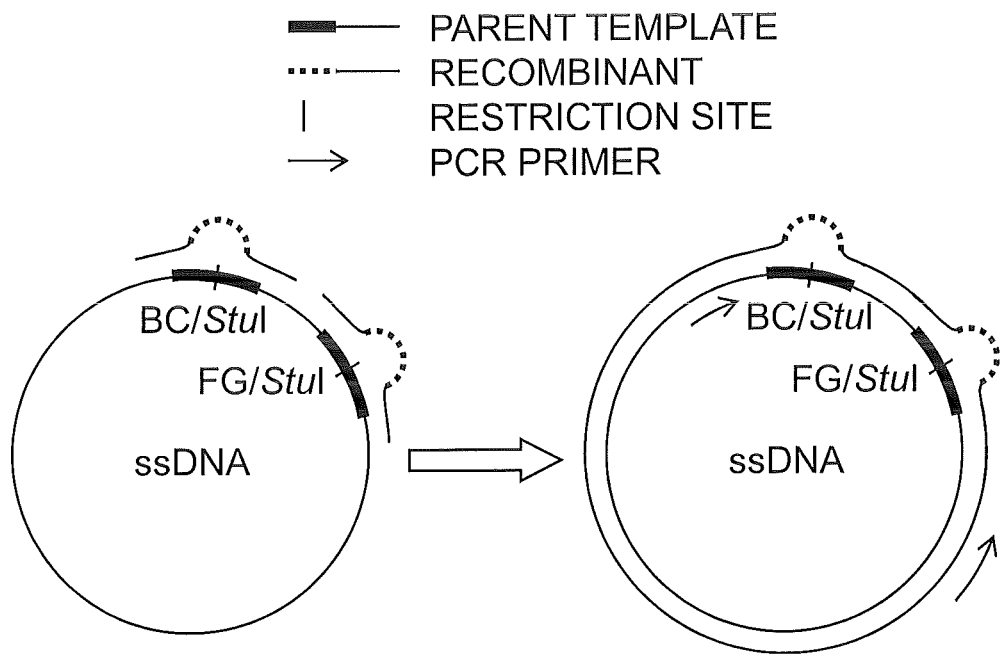
FIG. 3 depicts the primer extension reaction used in the generation of the ribosome-display library. The BC loop and FG loop oligonucleotides are annealed to the single-stranded ribosome-display vector (ssDNA), which contains nucleic acids encoding FN3. The primers are extended using polymerase and ligase to complete the heteroduplex (cccDNA). PCR primers used in the generation of the ribosome-display template are indicated by arrows.

A large library of Fibronectin III monobodies (FN3) was constructed by annealing triplet codon oligonucleotides to the BC and FG variable loops of a single-stranded DNA plasmid containing the necessary components for ribosome-display (pRDV-FN3-M13 Ori-StuI, FIG. 2). Oligonucleotides with a bias toward insertion of codons for Tyrosine (30%), Glycine (15%), and Serine (15%), were synthesized with varying numbers of triplet codons resulting in 5, 6, 7, and residues for the BC loop and 7, 9, 10, 11, 12, and 13 residues for the FG loop (Fellouse, et al. (2004) Proc. Natl. Acad. Sci. USA 101:12467-12472; Gilbreth & Koide (2012) Curr. Opin. Struct. Biol. 22:413-420). These biases were chosen because of evidence of a high percentage of Tyrosine residues at variable regions of various affinity reagents (Mian, et al. (1991) J. Mol. Biol. 217:133-151; Zemlin, et al. (2003) J. Mol. Biol. 334:733-749). It is thought that the prevalence of Tyrosine at interaction sites is attributed to the many types of tight bonds the side-group can form with residues of an antigen. The surrounding Glycine and Serine residues allow for flexibility of the Tyrosine side chain and therefore optimal contact (Koide & Sidhu (2009) ACS Chem. Biol. 4:325-334). After primer extension, the closed-circular DNA or cccDNA heteroduplex is formed which appears as a double-stranded DNA plasmid when run on an agarose gel (FIG. 3). Comparing the ds pRDV control to the newly formed cccDNA shows similar bands at about 6 kbp and at 2 kbp indicating double-stranded DNA was formed and the primer extension was a success. The single-stranded pRDV was completely converted to cccDNA and all of the megaprimers were annealed. The cccDNA was subsequently used as the template for a large scale PCR.

EXAMPLE 3

Phage-TolA Recombinant Confirmation

To confirm the cccDNA library's viability and recombination rate, an assay was developed, which takes advantage of the TolA tether region of the ribosome-display vector as a tag for phage binding and detection of the monobody. This protein tether is present to allow the nascent monobody to completely emerge from the ribosomal tunnel during translation (Pluckthun (2012) Methods Mol. Biol. 805:3-28; Dreier & Pluckthon (2011) Methods Mol. Biol. 687:283-306). It has been identified as a periplasmic coreceptor for bacteriophage infection of E. coli (Riechmann & Holliger (1997) Cell 90:351-360). The phage coat protein pIII was shown to bind to the TolA C-terminus of the cell during infection. The C-terminus of the TolA constitutes the tether. A small amount of the cccDNA was transformed and 96 colonies were picked and grown. After induction with IPTG and concomitant infection with helper phage, the FN3 monobody-FLAG-TolA fusion was expressed along with the M13 bacteriophage. Immobilization of anti-FLAG-monoclonal antibody captured the FN3 fusion with TolA bound by the phage. The phage coat protein was then detected using an anti-M13 HRP-conjugated antibody in an ELISA. The recombination rate was determined to be about 40%. This is likely an underestimation since 70% of the Sanger sequencing chromatograms showed two or more different plasmids per isolate that could not be completely deciphered. Calculations were then be made for the appropriate degree of PCR amplification required to maintain the desired diversity.

EXAMPLE 4

FN3 Ribosome-Display Library Template

The large-scale PCR resulted in two expected species as the coding strand contained the recombinant sequence, while the non-coding strand was the parental strand. Both strands were amplified in the PCR because the primers could not discriminate between the two when hybridizing at the ends of the constant scaffold. To target the unwanted parental strand for destruction, the amplification reaction was digested with StuI, which digested the parental strand containing the BC and FG loops that were lacking in the recombination sequence. The undigested recombinant strand was separated and extracted by gel electrophoresis. A single product expected at 710 bp resulted from the PCR, which included the two species. Fully and partially digested fragments were expected at 514 bp (1 cut at BC), 360 bp (2 cut), 350 bp (1 cut at FG), 197 bp and 153 bp (both 2 cut). The uncut recombinant band at 710 bp band was gel extracted and used for a second round of large scale PCR.

To obtain a large library size, 24 pmol or ~$1.5 \times 10^{13}$ molecules of DNA was purified for ribosome-display template. Additional PCR amplification yielded ~430 pmol or enough for 18 selections with a starting library diversity of $1.5 \times 10^{13}$. This could theoretically be amplified without loss of diversity assuming no PCR bias. Little bias was plausible because of the constant monobody scaffold. The above effort could be compared to constructing a phage-display library where maintaining a smaller library of $7 \times 10^{10}$ variants requires growing 10 L of cells that then need to be infected, and the phage purified before storage at −80° C. in glycerol.

EXAMPLE 5

PExSR Selection for MAP2K5

For the first selection attempt using the newly constructed library, biotinylated human Mitogen Activated Protein Kinase Kinase 5 (MAP2K5) was used as a Target because of the many antibodies it has elicited in the past. To form the complex, the standard procedure (Dreier & Pluckthun (2012) In:*Ribosome-display and Related Technologies*, Douthwaite & Jackson, eds. Springer, New York, pp 261-286) was modified and a coupled in vitro transcription and translation (IVTT) kit (Kuchař, et al. (2014) *Proteins* 82(6): 975-89) was used with >$1.5 \times 10^{13}$ template DNA molecules. The PUREXPRESS IVTT kit from NEB was selected because the PURE system lacks nucleases and release factors (Shimizu, et al. (2001) *Nat. Biotechnol.* 19:751-755), has shown to form highly stable ternary complexes (Matsuura, et al. (2007) *Biochem. Biophys. Res. Commun.* 352: 372-377), contains a known ribosome concentration of 60 pmol or $3.6 \times 10^{13}$ molecules, and has been used in ribosome-display of an scFv (Ohashi, et al. (2007) *Biochem. Biophys. Res. Commun.* 352:270-276). The ribosome concentration was the potential bottle-neck of the translated library diversity. The selection was allowed to proceed in-solution so dimers would not be favorably selected. The complex of RNA-Ribosome-FN3-MAP2K5 was pulled down with streptavidin magnetic beads. After washing and elution of the complex, the recovered RNA was reverse transcribed and PCR amplified.

Success of the selection was monitored by comparing band intensity to a no Target control on an agarose gel. A greater intensity was seen with +Target as compared to the control. There was some non-specific binding observed with the −Target controls but the product recovery was significantly less. The positive control using the starting DNA template in the PCR showed the expected size of the megaprimer at about 285 bp. In this case, the full 710 bp template was amplified as well. Although the inside primers included in the PCR only amplified a 285 bp region, primers used in the PCR of the library construction (T7B and tolAk) were carried over even after purification steps, to prime a larger region. Bands resulting from the combinations of the outside and inside primers were observed in between at the expected sizes.

The post-ribosome-display round (RD1) PCR output was the megaprimer for annealing to a single-stranded uracilated phagemid in a step referred to as Primer Extension for Selection Rescue (PExSR; a term also used to define the entire method) to convert to the phage-display format. While transformation into *E. coli* should destroy any non-recombinant uracilated phagemid, this was not the case. A large percentage of the transformants were found to have the unwanted parental plasmid. As such, only 5% were recombinant, resulting in a recovery of $2.5 \times 10^7$ recombinant clones. The non-recombinants contained the StuI site and stop codons in the loops. Thus, the non-recombinants were not displayed and did not interfere with the selection.

Figure 4:
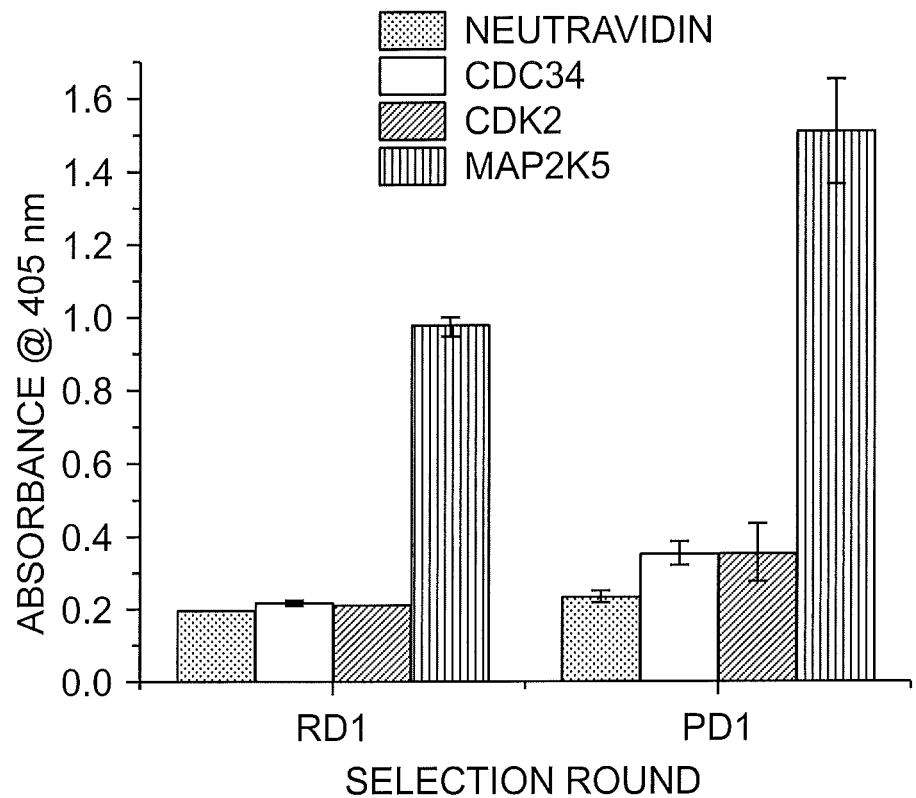
FIG. 4 shows the results of polyclonal and monoclonal ELISA after the first two rounds of PExSR. After the ribosome-display selection round (RD1), enrichment was observed. Following the phage-display round (PD1), the binding monobodies were further enriched. Sixty colonies were evaluated for the RD1 round and 12 for the PD1 round.

The second round of selection (PD1) was completed using phage-displayed clones in a similar manner to the ribosome-display round except that a competitor, in the form of a non-biotinylated Target MAP2K5 protein, was added at a 10-fold molar concentration. Any weak binders that had fast off-rates were bound by the high concentrations of competitor and therefore were not recovered. The selection progress was monitored by polyclonal and monoclonal ELISAs (FIG. 4). The signal increased as the best binding monobodies were enriched. There was binding observed in the polyclonal ELISA after the ribosome-display round. The signal then increased after the first round of phage-display. The monoclonal ELISA identified 1-2 binders after the ribosome-display round, but it represented only 5% of the 60 colonies picked. After the phage-display selection, the binders were greatly enriched to 85% of the 12 isolated colonies available for analysis. As such, the PD rounds are desirably carried out.

The final round of selection included 100-fold molar concentration of competitor. Four of the best clones were identified in a final monoclonal ELISA and were found to be unique after sequence analysis. A contaminant was discovered in the sequencing that represented about 50% of the recovered clones. This contaminant was identified as a high affinity anti-MAP2K5-FN3, which was developed through phage-display and affinity maturation selection performed elsewhere in the laboratory. The clone contained two cysteine residues as well as codons not found in the trinucleotide oligos, and therefore, did not arise independently. Antigen stocks were identified as the likely source of the contamination.

Cloning of the unique PExSR monobodies into *E. coli* SUMO fusion expression vectors gave protein yields of 5-10 mg/L. When tested against other proteins (e.g., BSA, CDC34 and CDK2), the anti-MAP2K5 clones (G4 and H1, provided under SEQ ID NOs: 8 and 9, respectively) were functional and specific to MAP2K5. To determine a rough estimate of binding constants, competition ELISAs were employed where many monobodies can be assayed in parallel at a low cost. Using the Inhibitory Concentration at 50% level (IC$_{50}$) as the measure of binding affinity, one monobody obtained through the PExSR method was compared with the best monobody from the traditional method of phage-display followed by error-prone PCR and affinity maturation. Using PExSR that took 8 days to complete, the binding constant of the best clone was around 0.5 nM, while the phage-display method, which took 21 days to complete, gave a binding constant of 3 nM.

EXAMPLE 6

Multiplexed Selection

It was subsequently determined whether the selection could be multiplexed by adding multiple Target proteins to the initial ribosome-display selection round, and then separating the specific binders in the subsequent phage-display rounds. Three human target proteins for the selection were chosen based on a range of difficulty to generate antibodies: COP9 Signalosome Subunit 5 (COPS5), Ubiquitin Specific Peptidase 11 (USP11), and Cyclin-Dependent Kinase 2. To expose the Targets to a large library, three times the number of library members were used in three combined in vitro transcription and translation reactions. The theoretical diversity of the ribosome-displayed monobodies was >4×10$^{13}$.

Figure 5A:
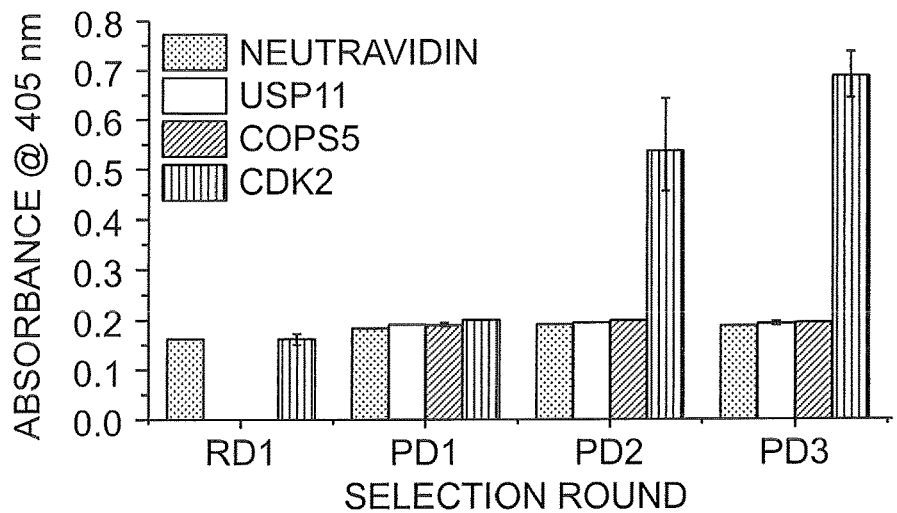
FIGS. 5A-5C shows ELISA results of multiplexed selection of three target proteins. Four rounds of selection were performed. RD1 contained a mix of the three antigens (COPS5, CDK2 and USP11). PD1 was used as a separation round with low stringency selection pressure. PD2 and PD3 included off-rate competition. The graphs show enrichment of monobodies to CDK2 (FIG. 5A), COPS5 (FIG. 5B) and USP11 (FIG. 5C) after the separation round.
Figure 5B:
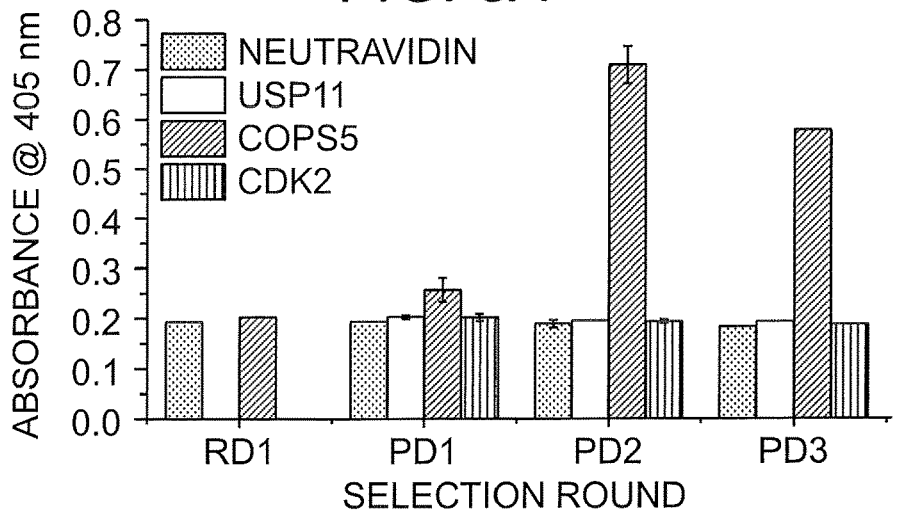
Figure 5C:
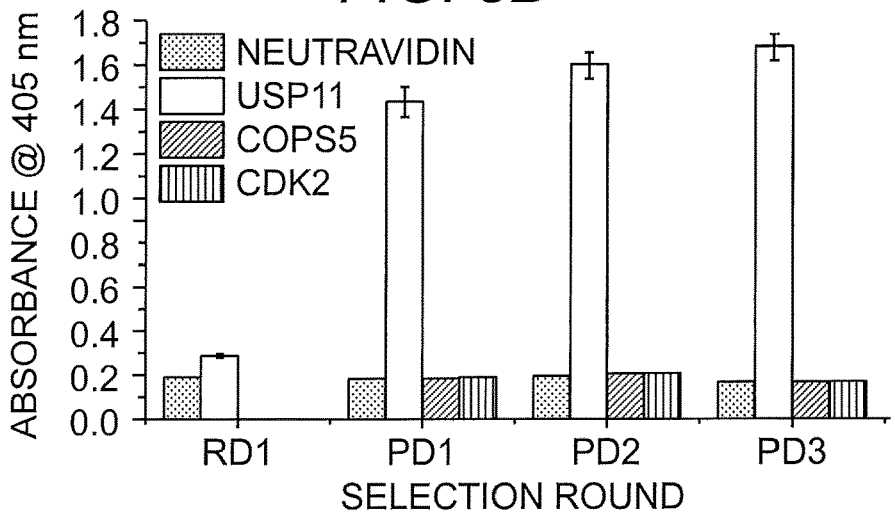
Figure 6:
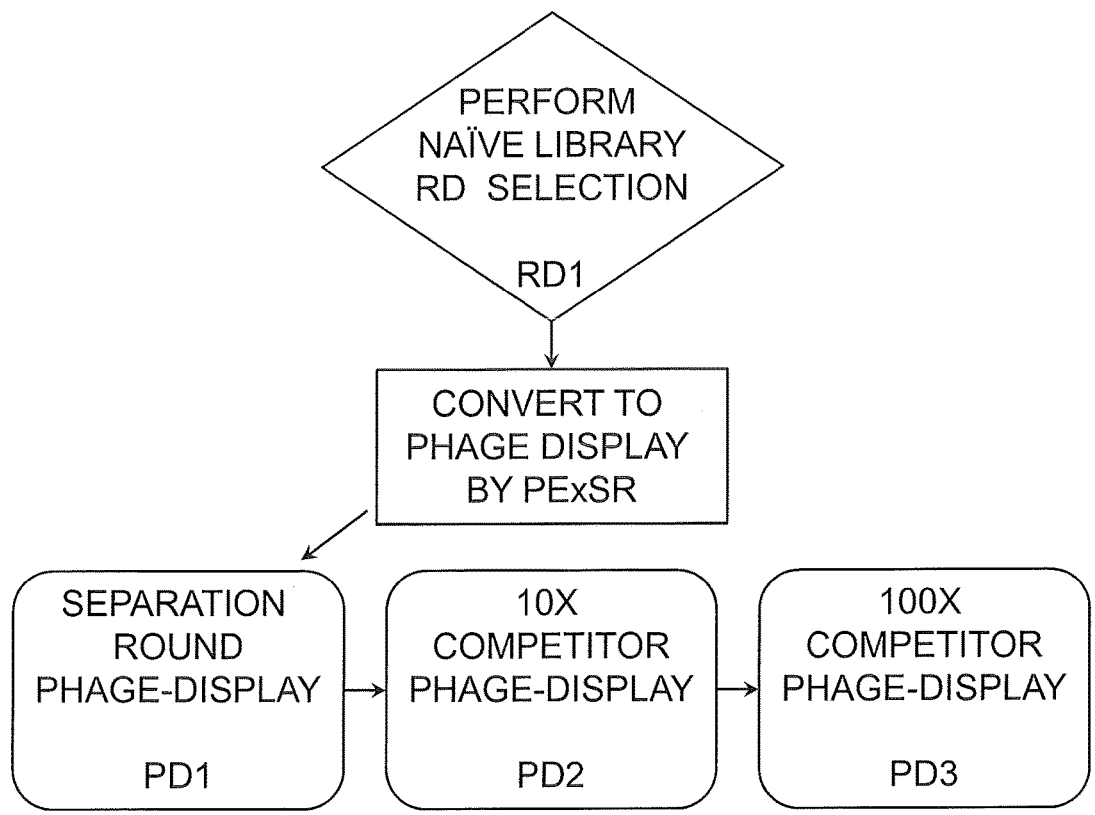
FIG. 6 provides a flow chart of the multiplexed selection of binding agents using the PExSR method.

The ribosome-display round (RD1) and PExSR were performed as described earlier. The conversion library was estimated to be >4×10$^8$ clones. The first phage-display round (PD1) was of low stringency with the Targets now separated. The second (PD2) and third round (PD3) included off-rate selections with 10-fold and 100-fold excess competitor. The enrichment of monobodies to each Target through the rounds could be seen in polyclonal ELISAs (FIGS. 5A-5C). As expected, the tightest binding monobodies were selected and enriched as the selection progressed, which translated to greater signal intensity. After the second round of phage-display (PD2), further selection rounds gained modest improvements in binding affinity as can be detected by ELISA signal intensity. Competition ELISAs showed a rough estimate of binding constants. Two monobodies with unique sequences were found that bound to the COPS5 Target with IC$_{50}$ values of ~3 nM. Similarly, two different monobodies were found to bind to USP11 with IC$_{50}$ values of ~10 nM. The CDK2 selection resulted in only one unique sequence with an IC$_{50}$ value of ~7 nM.

To get a better determination of the binding kinetics, Isothermal Titration calorimetry was performed on select FN3 monobodies. The USP11 monobody gave excellent exothermic heat change. The ITC resulted in a K$_D$ of 6±2.27 nM for the B7 clone and a K$_D$ of 3.76±1.66 nM for the C9 clone. The binding constants were within 2-fold of the estimated K$_D$s as determined by the IC$_{50}$ of the competition ELISA. This agreement indicated that the IC$_{50}$ estimations of the remaining clones were also in close accordance with the actual binding constant (Table 2).

TABLE 2

| FN3 | Clone | Estimated IC$_{50}$[a] (nM) | ITC K$_D$[b] (nM) |
|---|---|---|---|
| Anti-MAP2K5 | H1 | 0.5 | n.d. |
| Anti-CDK2 | E1 | 7 | n.d. |
| Anti-COPS5 | E4 | 3 | n.d. |
| Anti-COPS5 | G6 | 3 | n.d. |
| Anti-USP11 | B7 | 10 | 6 ± 2.27 |
| Anti-USP11 | C9 | 10 | 3.76 ± 1.66 |

[a]IC$_{50}$ is the inhibitory concentration at 50%, which is used here as an estimate of binding affinity.
[b]ITC, isothermal tritration calorimetry was performed for the USP11 monobodies. KD is the equilibrium binding constant.
n.d., not determined.

EXAMPLE 7

Selection of FHA Mutants

Nucleic acids encoding the N-terminal FHA1 domain of yeast Rad53p, which binds to a Myc-pT phosphopeptide (Pershad, et al. (2012) *J. Mol. Biol.* 424:88-103) were mutated by error-prone PCR using nucleotide analogs and cloned into ribosome-display vector pRDV. Twenty-four clones were sequenced and 17 were found to have mutations. Based upon the average mutations per sequence, the overall mutation rate per 1000 bases was found to be 0.32%. In accordance with the instant method, the ribosome display library was amplified (e.g., using primers T7B and TolAk), and 5×10$^{11}$ molecules were subjected to in vitro transcription/translation. Displayed FHA mutants were selected for binding to biotinylated Myc dual phosphorylated peptide and immobilized with streptavidin-coated magnetic beads.

After FHA mutant capture, mRNA of interest were reverse-transcribed and the resulting cDNA was subject to PCR for 35 cycles using primers specific for FHA. The resulting products (512 bp) were then annealed to a single-stranded phage-display vector, PExSR was conducted, and FHA mutants were displayed and selected for binding to the biotinylated Myc dual phosphorylated peptide. Approximately 2.18×10$^8$ recombinant clones were obtained.

In round 1 phage-display selection (PD1), competitor peptide (i.e., non-biotinylated Myc dual phosphorylated peptide) was added at a 10-fold molar concentration, complexes were washed to remove 99.999% of the phage, and 8.8×10$^5$ phage were recovered. In Round 2 (PD2), competitor peptide was added at a 100-fold molar concentration, complexes were washed, and 1×10$^7$ phage were recovered. In the final round (PD3), competitor peptide was added at a 1000-fold molar concentration, complexes were washed, and 1×10$^7$ phage were recovered.

Figure 7:
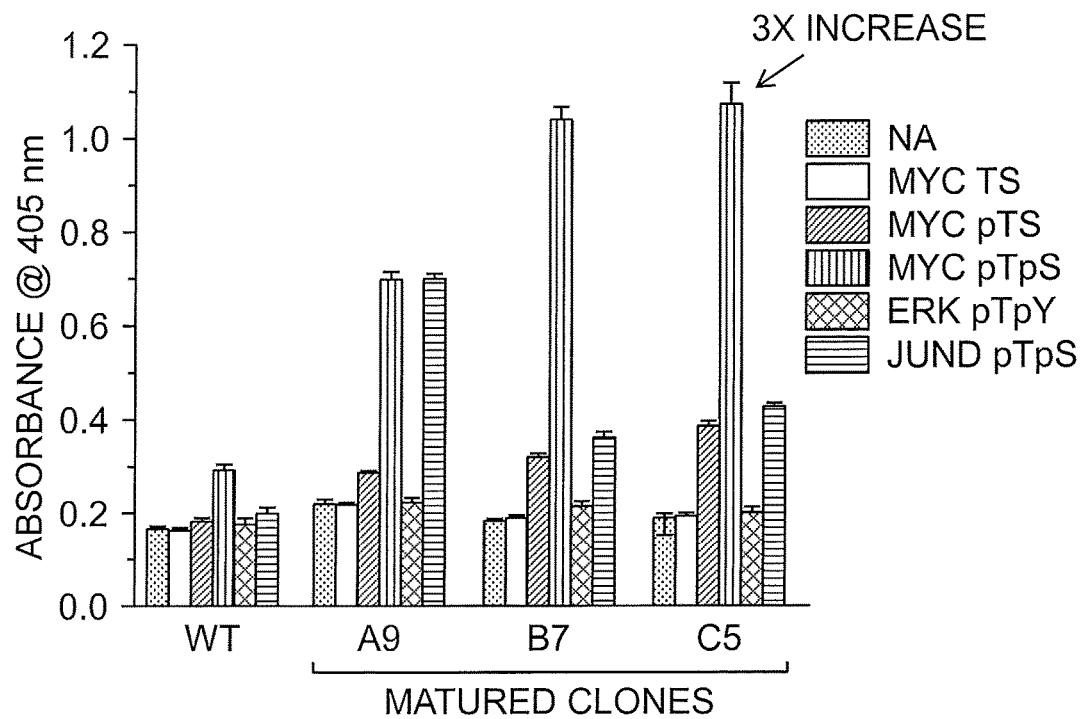
FIG. 7 shows reactivity of matured Forkhead-Associated (FHA) domain clones for unphosphorylated Myc (Myc TS), phosphothreonine Myc (Myc pTS), dual phosphorylated Myc (Myc pTpS), dual phosphorylated ERK1/2 (ERK pTpY), and dual phosphorylated JunD (JunD pTpS) as determined by ELISA.

There of the recovered clones were tested for reactivity with unphosphorylated Myc (KKFELLPTPPLSPSY; SEQ ID NO:10), phosphothreonine Myc (KKFELLPpTPPL-SPSY; SEQ ID NO:11), dual phosphorylated Myc (KK-FELLPpTPPLpSPSY; SEQ ID NO:12), dual phosphorylated ERK1/2 (HTGFLpTEpYVATRW; SEQ ID NO:13), and dual phosphorylated JunD (EARSRDApTPPVpSPINYK; SEQ ID NO:14) and it was found that the matured clones exhibited limited cross-reactivity (FIG. 7).

What is claimed is:

1. A method for generating high affinity monobodies to a target molecule comprising:
   (a) annealing a first population of oligonucleotides and a second population of oligonucleotides, each encoding a library of binding sites, to a single-stranded ribosome-display vector comprising nucleic acids encoding a monobody scaffold;
   (b) primer extending the first population of oligonucleotides and second population of oligonucleotides to generate heteroduplexes, wherein one strand of the heteroduplexes encodes the monobody scaffold comprising the library of binding sites;
   (c) amplifying both strands of the heteroduplexes;
   (d) subjecting the amplified products of step (c) to in vitro transcription and in vitro translation to produce ribosome-mRNA-monobody scaffold complexes;
   (e) contacting the ribosome-mRNA-monobody scaffold complexes with one or more tagged target molecules to bind the ribosome-mRNA-monobody scaffold complexes to the tagged target molecules;
   (f) removing unbound ribosome-mRNA-monobody scaffold complexes;
   (g) dissociating the ribosome-mRNA-monobody scaffold complexes bound to the tagged target molecules;
   (h) reverse transcribing the mRNA molecules of (g) to generate cDNA;
   (i) amplifying the cDNA molecules of (h) with primers that anneal to nucleic acids encoding the monobody scaffold to generate amplified nucleic acids encoding the monobody scaffold and binding sites;
   (j) annealing the amplified nucleic acids of (i) to a phage-display vector comprising nucleic acids encoding the monobody scaffold;
   (k) primer extending the annealed nucleic acids of (j) to generate heteroduplexes, wherein one strand of the heteroduplexes encodes the monobody scaffold and binding sites;
   (l) expressing the monobody scaffold and binding sites encoded by the phage-display vector; and
   (m) screening the expressed products of (l) with one or more of the tagged target molecules thereby generating high affinity monobodies to the one or more target molecules.

2. The method of claim 1, in which the first population of oligonucleotides comprise a BC loop with the nucleotide sequence of SEQ ID NO:15.

3. The method of claim 1, in which the second population of oligonucleotides comprise a FG loop with the nucleotide sequence of SEQ ID NO:16.

4. The method of claim 1, in which the monobody comprises the amino acid sequence of SEQ ID NO:1 or SEQ ID NO:2.

* * * * *